United States Patent [19]

Tam

[11] Patent Number: 5,786,327
[45] Date of Patent: Jul. 28, 1998

[54] BONE STIMULATING FACTOR, METHODS OF ISOLATING SAME, AND METHODS OF INCREASING BONE GROWTH COMPRISING ADMINISTERING SAME

[75] Inventor: Cherk Shing Tam, Oakville, Canada

[73] Assignee: Gensci Regeneration Sciences Inc., Mississauga, Canada

[21] Appl. No.: 302,485

[22] Filed: Sep. 12, 1994

Related U.S. Application Data

[63] Continuation-in-part of Ser. No. 120,217, Sep. 13, 1993, abandoned, which is a continuation-in-part of Ser. No. 31,386, Mar. 12, 1993, abandoned.

[51] Int. Cl.$^6$ .......................... C07K 1/14; C07K 14/51; A61K 38/18
[52] U.S. Cl. .................. 514/12; 530/300; 530/350; 530/399; 530/412
[58] Field of Search .................. 530/300, 399, 530/412, 350; 514/12

[56] References Cited

U.S. PATENT DOCUMENTS

| | | | |
|---|---|---|---|
| 4,320,118 | 3/1982 | White et al. | 530/328 |
| 4,877,864 | 10/1989 | Wang et al. | 530/324 |
| 5,011,691 | 4/1991 | Oppermann et al. | 424/423 |
| 5,461,034 | 10/1995 | Rodan et al. | 514/21 |

OTHER PUBLICATIONS

Bowie et al. Science 247 1306–1310, 1990.
Ngo et al. The Protein Folding Problem and Tertiary Structure Prediction. Merz et al, eds., Birkhauser, Boston, pp. 491–495, 1994.
Rudinger et al. Peptide Hormones. Parsons, eds., University Park Press, Baltimore, pp. 1–7, 1976.
Navab et al. "Rat Plasma Prealbumin", *J. Biol. Chem.* 252(14): 5100–5106, (Jul. 1977).
Sundelin et al. "The Primary Structure of Rabbit and Rat Prealbumin . . . " *J. Biol. Chem.* 260(10):6481–6487 (May 1985).

Primary Examiner—David L. Fitzgerald
Assistant Examiner—Elizabeth C. Kemmerer
Attorney, Agent, or Firm—Foley & Lardner

[57] ABSTRACT

A polypepide substance isolated from rat serum which, upon administration to rats incapable of producing PTH (parathyroidectomized rats), produces an increase in the observed bone mineral apposition rate. The substance has been isolated in two forms, a first larger polypeptide having a molecular weight about twice that of a second smaller polypeptide. The first eleven amino acids of the sequence of the smaller polypepeptide have been determined to be Gly Pro Gly Gly Ala Gly Glu Thr Lys Pro Ile (SEQ ID NO:3). The first seven amino acids of the larger polypeptide have been determined to be Gly Pro Gly Gly Ala Gly Glu (SEQ ID NO:2). The larger polypeptide might be the dimer of the smaller peptide. A nucleic acid probe, based on the amino acid sequence of the rat peptide was used to screen a human liver cDNA fetal library. A polypeptide was thus chemically synthesized according to the sequence Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO: 11). The bone apposition rate in rats increases in a dose dependent fashion upon administration of this chemically synthesized compound. A modified polypeptide containing a cysteine→alanine substitution was carried synthesized: Glr Ile Gly Lys Arg Thr Asn Glu His Thr Ala Asp Ala Lys Ile Lys Pro Asn Thr Leu His Lys Lys Ala Ala Glu Thr Leu Met Val Leu Asp Gin Asn Gin Pro (SEQ ID NO: 13). Some of the bone stimulatory effects of the normal polypeptide were found for the modified polypeptide.

57 Claims, 20 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:1:

```
Gly Pro Gly Gly Ala Gly Glu Thr Lys Pro Ile
 1           5                   10
```

(2) INFORMATION FOR SEQ ID NO:2:

(i) SEQUENCE CHARACTERISTICS:
        (A) LENGTH: 7 amino acids
        (B) TYPE: amino acid
        (D) TOPOLOGY: linear (x i) SEQUENCE DESCRIPTION: SEQ ID NO:2:

```
Gly  Pro  Gly  Gly  Ala  Gly  Glu
 1                 5
```

(2) INFORMATION FOR SEQ ID NO:3:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (x i) SEQUENCE DESCRIPTION: SEQ ID NO:3:

```
GGY  CCY  GGY  GGY  GCY  GGY  GAR  ACY  AAR  CCY  AT        32
Gly  Pro  Gly  Gly  Ala  Gly  Glu  Thr  Lys  Pro
 1                 5                      10
```

(2) INFORMATION FOR SEQ ID NO:4:

(i) SEQUENCE CHARACTERISTICS:
        (A) LENGTH: 10 amino acids
        (B) TYPE: amino acid
        (D) TOPOLOGY: linear (x i) SEQUENCE DESCRIPTION: SEQ ID NO:4:

```
Gly  Pro  Gly  Gly  Ala  Gly  Glu  Thr  Lys  Pro
 1                 5                      10
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:5:

```
AAG  CTT  CAC  ACC  ACG  AAC  CAG                           21
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (x i) SEQUENCE DESCRIPTION: SEQ ID NO:6:

```
TTA  TGA  GTA  TTT  CTT  CAA  GGG                           21
```

(2) INFORMATION FOR SEQ ID NO:7:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (i i) MOLECULE TYPE: cDNA to mRNA (x i) SEQUENCE DESCRIPTION: SEQ ID NO:7:

```
TTTGGCTTTA TTCATAGCGG TAATTAATGA TCAAGACAGT TGATTACTCG TAAGCACTAT        60

TAAAAATTTG CA ATG ACT GCT CAA AAT ACA GAC CTT AAC CAA CTA TCC          108
              Met Thr Ala Gln Asn Thr Asp Leu Asn Gln Leu Ser
              1               5                   10

AAC AGT TTC ACT TTA GGG ATC GGA AAA CGA ACA AAT GAA CAT ACG GCA        156
Asn Ser Phe Thr Leu Gly Ile Gly Lys Arg Thr Asn Glu His Thr Ala
            15              20                  25

GAT TGT AAA ATT AAA CCG AAC ACC TTG CAT AAA AAA GCT GCA GAG ACT        204
Asp Cys Lys Ile Lys Pro Asn Thr Leu His Lys Lys Ala Ala Glu Thr
        30              35                  40

TTA ATG GTC CTT GAC CAA AAT CAA CCA TAAAGGATCT GCAGCTTATG              251
Leu Met Val Leu Asp Gln Asn Gln Pro
45              50

TCTTCTAGTT TATCTTTTGC ATAAAAAGC TGCAGAGACT TTAATGGTAA TTGCCAAAAT       311

CAACCATAAA GGATCTGC                                                    329
```

( 2 ) INFORMATION FOR SEQ ID NO:8:

( i ) SEQUENCE CHARACTERISTICS:
        ( A ) LENGTH: 53 amino acids
        ( B ) TYPE: amino acid
        ( D ) TOPOLOGY: linear ( x i ) SEQUENCE DESCRIPTION: SEQ ID NO:8:

```
Met Thr Ala Gln Asn Thr Asp Leu Asn Gln Leu Ser Asn Ser Phe Thr
1               5                   10                  15

Leu Gly Ile Gly Lys Arg Thr Asn Glu His Thr Ala Asp Cys Lys Ile
            20                  25                  30

Lys Pro Asn Thr Leu His Lys Lys Ala Ala Glu Thr Leu Met Val Leu
        35                  40                  45

Asp Gln Asn Gln Pro
        50
```

( 2 ) INFORMATION FOR SEQ ID NO:9:

( i ) SEQUENCE CHARACTERISTICS:
        ( A ) LENGTH: 145 base pairs
        ( B ) TYPE: nucleic acid
        ( C ) STRANDEDNESS: single
        ( D ) TOPOLOGY: linear ( i v ) ANTI-SENSE: no ( x i ) SEQUENCE DESCRIPTION: SEQ ID NO:9:

```
AATTCTTAGG ATCCTAGGAT G GGG ATC GGA AAA CGA ACA AAT GAA CAT ACG         51
                         Gly Ile Gly Lys Arg Thr Asn Glu His Thr
                         1               5                   10

GCA GAT TGT AAA ATT AAA CCG AAC ACC TTG CAT AAA AAA GCT GCA GAG         99
Ala Asp Cys Lys Ile Lys Pro Asn Thr Leu His Lys Lys Ala Ala Glu
            15              20                  25

ACT TTA ATG GTC CTT GAC CAA AAT GAA CCA TAAAGATCTT GATCGA              145
Thr Leu Met Val Leu Asp Gln Asn Gln Pro
        30                  35
```

( 2 ) INFORMATION FOR SEQ ID NO:10:

( i ) SEQUENCE CHARACTERISTICS:
        ( A ) LENGTH: 137 base pairs
        ( B ) TYPE: nucleic acid
        ( C ) STRANDEDNESS: single
        ( D ) TOPOLOGY: linear ( i v ) ANTI-SENSE: yes (x i) SEQUENCE DESCRIPTION: SEQ ID NO:10:

```
TCAAGATCTT  TATGGTTCAT  TTTGGTCAAG  GACCATTAAA  GTCTCTGCAG  CTTTTTTATG        60
CAAGGTGTTC  GGTTTAATTT  TACAATCTGC  CGTATGTTCA  TTTGTTCGTT  TTCCGATCCC       120
CATCCTAGGA  TCCTAAG                                                         137
```

(2) INFORMATION FOR SEQ ID NO:11:

(i) SEQUENCE CHARACTERISTICS:
        (A) LENGTH: 36 amino acids
        (B) TYPE: amino acid
        (D) TOPOLOGY: linear (x i) SEQUENCE DESCRIPTION: SEQ ID NO:11:

```
Gly  Ile  Gly  Lys  Arg  Thr  Asn  Glu  His  Thr  Ala  Asp  Cys  Lys  Ile  Lys
 1              5                        10                       15
Pro  Asn  Thr  Leu  His  Lys  Lys  Ala  Ala  Glu  Thr  Leu  Met  Val  Leu  Asp
               20                        25                       30
Gln  Asn  Gln  Pro
               35
```

(2) INFORMATION FOR SEQ ID NO:12:

(i) SEQUENCE CHARACTERISTICS:
        (A) LENGTH: 36 amino acids
        (B) TYPE: amino acid
        (D) TOPOLOGY: linear (i x) FEATURE:
        (A) NAME/KEY: Modified site
        (B) LOCATION: ...2
        (D) OTHER INFORMATION: /note="Xaa is N-acetyl glycine"

(x i) SEQUENCE DESCRIPTION: SEQ ID NO:12:

```
Xaa  Ile  Gly  Lys  Arg  Thr  Asn  Glu  His  Thr  Ala  Asp  Cys  Lys  Ile  Lys
 1              5                        10                       15
Pro  Asn  Thr  Leu  His  Lys  Lys  Ala  Ala  Glu  Thr  Leu  Met  Val  Leu  Asp
               20                        25                       30
Gln  Asn  Gln  Pro
               35
```

(2) INFORMATION FOR SEQ ID NO:13:

(i) SEQUENCE CHARACTERISTICS:
        (A) LENGTH: 36 amino acids
        (B) TYPE: amino acid
        (D) TOPOLOGY: linear (x i) SEQUENCE DESCRIPTION: SEQ ID NO:13:

```
Gly  Ile  Gly  Lys  Arg  Thr  Asn  Glu  His  Thr  Ala  Asp  Ala  Lys  Ile  Lys
 1              5                        10                       15
Pro  Asn  Thr  Leu  His  Lys  Lys  Ala  Ala  Glu  Thr  Leu  Met  Val  Leu  Asp
               20                        25                       30
Gln  Asn  Gln  Pro
               35
```

BONE STIMULATING FACTOR, METHODS OF ISOLATING SAME, AND METHODS OF INCREASING BONE GROWTH COMPRISING ADMINISTERING SAME

This is a continuation-in-part of application Ser. No. 08/120,217 filed Sep. 13, 1993 now abandoned, which is a continuation-in-part of application Ser. No. 08/031,386 filed Mar. 12, 1993, now abandoned. The specifications of both of these prior applications are incorporated herein by reference.

FIELD OF THE INVENTION

The present invention relates to proteins and polypeptides which stimulate bone growth.

BACKGROUND OF THE INVENTION

It is known that even in the adult human, bone can be subject to turnover. In certain locations, such as the internal auditory capsule, there is apparently no turnover after the organ is formed. In other locations, particularly in the central skeletal axis, the turnover appears to continue during adulthood. Bone turnover occurs on the surface of the existing bone matrix, which is composed of protein (mainly collagen) and minerals. Bone turnover is initiated with the destruction of bone matrix by osteoclasts. An osteoclast is a multinucleated cell which secretes acid and proteolytic enzymes leading to the lysis of the collagen matrix protein and the release of minerals into the extracelluar fluid compartment. Following this initial phase of bone destruction, or resorptive phase, formation of new bone protein matrix sets in. New bone proteins are deposited, and sometime later, minerals begin to be incorporated into the newly formed matrix. The formation of bone matrix and its subsequent mineralization are functions of osteoblasts, which are mononucleated cells. The formation phase is often followed by a period of inactivity (1,2). Resorption appears to be tightly coupled with formation (3) in vivo. Bone turnover is thus a succession of events, the location of which is known as the Bone Metabolism Unit or the BMU. Osteoblasts and osteoclasts, the putative mediators of bone turnover are thought to belong to two distinct cell lineages. These two cell types are not preformed cells, but they differentiate from their precursors through cell activation (4,5,6).

Bone matrix can either be maintained by a total cessation of bone turnover, as for the bone of the internal auditory capsule, or by a balance between formation and resorption. In many studies on skeletal changes in relation to age, a gain in the total body bone volume is observed during the growth period and the skeletal mass reaches a maximum at early adulthood. This gain is followed by a fall in bone volume as age advances. In females, a phase of more rapid bone loss often occurs during the perimenopausal period before a slower steadier phase. For this reason, bone loss in the female tends to be more severe than in the male. An understanding of bone balance in the BMU may thus be critical to understanding the pathogenesis of skeletal aging. In any case, mechanisms controlling bone turnover are complex and are not well understood at this time. The complexity of the control mechanisms has resulted in a variety of approaches to reducing bone loss.

Generally speaking, bone turnover can be regulated at two different stages. It can be regulated at the stage of the activation of precursor cells. Regulators of cellular activation can control not only the number of active BMU in the skeleton, but possibly also the number of osteoclasts and osteoblasts in an individual BMU. Alternatively, bone turnover can be regulated at the level of differentiated bone cells. The complexity of the bone cell system makes the separate study of these two levels of regulation difficult (3).

Regulators of bone cells appear to fall into two categories. The first of these interacts with specific receptors on cell membranes. One class of these regulators acts through the adenylate cyclase system with the generation of intracellular cyclic AMP as a second messenger acting on the protein kinase K system. Parathyroid hormone (PTH) and calcitonin (CT) belong to this class (7). A second class also interacts with a membrane receptor and results in the intracellular release of a molecule derived from phosphoinositides which in turn leads to an increase in intracellular calcium and activation of Kinase C. A third class involves interaction of the regulator with a cell surface receptor, but the second signal is generated by the receptor molecule itself with the subsequent activation of tyrosine Kinase. Many of the growth factors appear to act in this way (8–15). The second category of regulator does not interact with a cell membrane receptor, but can cross the cell membrane to bind with a cytosolic receptor. The regulator is then transported across the nuclear membrane by the cytosolic receptor to interact with the DNA resulting in increased transcription of specific genes. Steroid hormones, including vitamin D, appear to act in this manner (16).

Many hormones stimulate the proliferation of osteoclasts. These include $1,25(OH)_2D$, PTH and prostaglandins. PTH and $1,25(OH)_2D$ receptors in osteoclasts have apparently not yet been identified. These two hormones seem to have no effect on osteoclasts in culture. However, when osteoclasts are co-cultured with osteoblast-like cell lines, PTH and $1,25(OH)_2D$ stimulate the proliferation of osteoclasts. IL-1 and TNF appear to act in a similar way as PTH and $1,25(OH)_2D$. Other growth factors, like EGF, TFG and PDGF appear to stimulate osteoclasts through increased production of PGE. Calcitonin and corticosteroids are known osteoclast inhibitors along with chemicals such as diphosphonates.

It is currently believed that interleukin 1 may stimulate collagen and non-collagen bone protein and DNA synthesis. The effect on bone protein synthesis is blocked by indomethacin, suggesting that this action of IL-1 is mediated through PGE. Indomethacin seems to have no effect on the IL-1 effect on osteoblast DNA synthesis. In culture studies on osteoblast-like cell lines suggest that some locally produced growth factors stimulate DNA and collagen synthesis. In bone cell culture, PTH or Vitamin D suppresses collagen synthesis. This in vitro effect of PTH contrasts with the in vivo effect observed in human subjects and experimental animals. It has been demonstrated in rats and in human hyperparathyroid patients that PTH can stimulate the deposition of mineralized bone matrix. Preliminary clinical trial studies on the efficacy of the PTH 1-34 amino acid fragment in the treatment of osteoporosis indicate that this PTH fragment can increase the trabecular volume. The reason for this discrepancy is not yet fully explained.

Parathyroid hormone is a peptide of 84 amino acids in its mature form. Initially translated pre-pro-parathyroid hormone is much larger, the pre sequence being a signal sequence which is cleaved when the peptide enters the rough endoplasmic reticulum. In the golgi apparatus, the pro-sequence is cleaved off leaving the intact mature hormone packaged in the secretory granule. It appears that regulation of the rate of secretion is governed not so much by the rate of production of the intracellular peptide, but in the rate of intracellular destruction and in the rate of secretion. Intracellularly, the mature peptide is truncated at both the amino and the carboxyl termini. The truncated peptide may be secreted into the circulation as an inactive fragment. The secretion of the mature peptide can be stimulated by a drop in the extracelluar calcium concentration. An elevated serum calcium concentration on the other hand appears to suppress the secretion of PTH. Once in circulation, the mature peptide is rapidly cleaved in the liver at many sites of the molecule including the region of the 38 amino acid residue. The smaller fragment at the amino terminal end, which includes the first 34 amino acids, carries the full known biological activity in terms of its action on the kidney, the intestine and the bone. It also binds fully to the cell membrane receptor to stimulate cAMP production. The level of the 1-38 fragment in the serum is normally unmeasurable indicating that it has a short circulatory life. The larger inactive carboxyl terminal fragment has a relatively long half life and carries the highest proportion of the immunoreactive PTH in the circulatory system. All fragments in circulation are eventually destroyed in the kidney and the liver. One of the renal mechanisms for ridding the circulating inactive PTH fragments is glomerular filtration (17).

PTH participates in calcium and skeletal homeostasis. PTH stimulates the tubular resorption of calcium by the kidney and inhibits the reabsorption of phosphate and bicarbonate by the proximal renal tubules. A second effect of PTH on the kidney is the stimulation of $1,25(OH)_2D$ production. This vitamin D metabolite is an in vivo stimulator of osteoclasts as well as an enhancer of intestinal calcium absorption. The increase in calcium absorption by the intestine following PTH stimulation is mediated by this vitamin D metabolite. In vivo, PTH stimulates osteoclastic bone resorption with the release of calcium into the circulation. PTH also causes proliferation of osteoblasts (18). In many cases of hyperparathyroidism there is a skeletal loss. However, an increase in spinal density has been reported in some cases of primary hyperparathyroidism (19,20,21) as well as in secondary hyperparathyroidism complicating renal failure. Kalu and Walker have observed that chronic administration of low doses of parathyroid extract led to sclerosis of bone in the rat (22). Tam et al. studied the effect of low calcium diet on the bone mineral apposition rate in the rat by tetracycline labelling and found that despite the loss of bone due to increase in bone resorption histologically (as a result of secondary hyperparathyroidism), the bone mineral apposition rate was increased (23). It was also found that the bone mineral apposition rate was increased in 23 human patients with mild primary hyperparathyroidism (24). After successful removal of parathyroid adenoma from four of the patients, the rate returned to the level observed in control subjects. There has also been found to be a dose dependent stimulation of the mineral apposition rate by PTH. The potency of the 1-34 fragment and the intact PTH hormone appears to be about the same on a molar basis. This is consistent with the 1-34 fragment of the PTH molecule carrying the biological activity of the intact hormone. It has also been observed that the end result of the administration of PTH on skeletal homeostasis depends on how the hormone is administered. For the same daily dose, the bone volume shows a dose dependent increase if the daily dose of the hormone is given as one single injection. However, when the same daily dose is administered by continuous infusion with a subcutaneous miniosmotic pump, the result is bone loss. Intermittent injection causes practically no effect on the serum calcium levels whereas infusion causes a dose dependent increase in the serum calcium. The effects of PTH administered by these two routes on bone mineral apposition rate as measured by tetracycline labelling are the same. What accounts for this differential effect is not understood (25).

Given the general understanding of bone growth and its regulation, various approaches to treatment of diseases involving reduction of bone mass and accompanying disorders are exemplified in the patent literature. For example, PCT Patent Application No. 9215615 published Sep. 17, 1992 describes a protein derived from a porcine pancreas which acts to depress serum calcium levels for treatment of bone disorders that cause elevation of serum calcium levels. European Patent Application No. 504938 published Sep. 23, 1992 describes the use of di- or tripeptides which inhibit cysteine protease in the treatment of bone diseases. PCT Patent Application No. 9214481 published Sep. 3, 1992 discloses a composition for inducing bone growth, the composition containing activin and bone morphogenic protein. European Patent Application No. 499242 published Aug. 19, 1992 describes the use of cell growth factor compositions thought to be useful in bone diseases involving bone mass reduction because they cause osteoblast proliferation. PCT Patent Application No. 4039656 published Jun. 17, 1992 describes a drug containing the human N-terminal PTH fragment 1-37. European Patent Application No. 451867 published Sep. 16, 1991 describes parathyroid hormone peptide antagonists for treating dysbolism associated with calcium or phosphoric acid, such as osteoporosis.

The relatively short half life of PTH in the blood serum and the relatively lengthy effect of intermittent PTH injection led the present investigator to the hypothesis that PTH may in some way lead to induction of a second factor into the circulatory system. The presence of such a second factor in blood serum of rats and of humans has thus been investigated.

It has been found possible to isolate from rat blood serum a polypeptide substance which, upon administration to rats incapable of producing PTH (parathyroidectomized rats), produces an increase in the observed bone mineral apposition rate. The desired polypeptide can be obtained from the isolated polypeptides by removing a polypeptide having a pI of about 9. It has further been observed that the bone apposition rate increases with the dose of the isolated substance administered, at least over the dose range and time period studied. The substance has been isolated in two forms, a first larger polypeptide having a molecular weight about twice that of a second smaller polypeptide. The first eleven amino acids of the sequence of the smaller polypeptide have been determined to be Gly Pro Gly Gly Ala Gly Glu Thr Lys Pro Ile (SEQ ID NO:1). The first seven amino acids of the larger polypeptide have been determined to be Gly Pro Gly Gly Ala Gly Glu (SEQ ID NO:2). The similarity of these two NH$_2$-terminal sequences has led to the proposition that the larger polypeptide might be the dimer of the first.

A nucleic acid probe, based on the amino acid sequence of the rat peptide has been synthesized and used to screen a human liver cDNA fetal library in order to isolate a human nucleic acid sequence coding for a human bone apposition polypeptide. A polypeptide was thus chemically synthesized according to the sequence Gly Ile Gly Lys Arg Thr Asn Glu His Thr Ala Asp Cys Lys Ile Lys Pro Asn Thr Leu His Lys Lys Ala Ala Glu Thr Leu Met Val Leu Asp Gln Asn Gln Pro (SEQ ID NO:11). It has been observed that the bone apposition rate in intact rats increases in a dose dependent fashion upon administration of this chemically synthesized compound. Reduced bone growth, normally observed for ovariectomized rats, was observed not to occur in rats after being administered with the polypeptide over a four week period beginning two weeks after ovariectomization. Bone calcium density was found to be maintained in ovariectomized rats administered with the polypeptide over an eight week period beginning eight weeks after ovariectormization.

It is thought possible that the active polypeptide is a dimer of the foregoing sequence, there being evidence of significant dimer formation, presumably due to a disulfide bridge between two polypeptides having the sequence shown.

A modified form of the polypeptide containing a cys→ala substitution was thus synthesized: Gly Ile Gly Lys Arg Thr Asn Glu His Thr Ala Asp Ala Lys Ile Lys Pro Asn Thr Leu His Lys Lys Ala Ala Glu Thr Leu Met Val Leu Asp Gln Asn Gln Pro (SEQ ID NO:13). Some of the bone stimulatory effects of the normal polypeptide were found for the modified polypeptide.

The bone mineral apposition rate in rats administered with rabbit antibodies to the normal polypeptide (SEQ ID NO:11) was found to be suppressed. The suppression was found to be attenuated in rats administered with both the normal polypeptide and antibodies to same.

BRIEF DESCRIPTION OF THE DRAWINGS

In the following description, reference is made to accompanying drawings, wherein.

The shaded area represents the lower epiphysis A section of the bone taken for measurement of bone apposition. The epiphyseal cartilage is indicated by arrow B.

Figure 20:
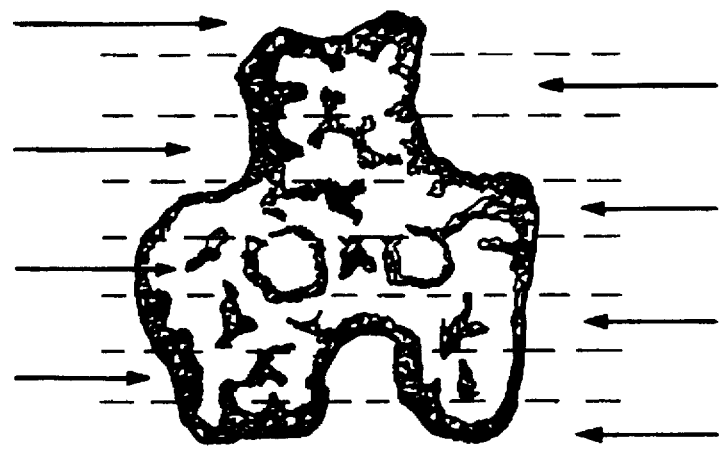

FIG. 20 shows a cross sectional view of the lower right femur of a rat. Bone apposition measurements were taken at thirty bone formation sites in the trabecular bone enclosed by the endosteal surface of the lower femoral epiphysis, the sectional area shown being systematically covered, the scanned sections being indicated by the dashed lines and the arrows indicating the movement of the microscope stage to cover the area.

Figure 21:
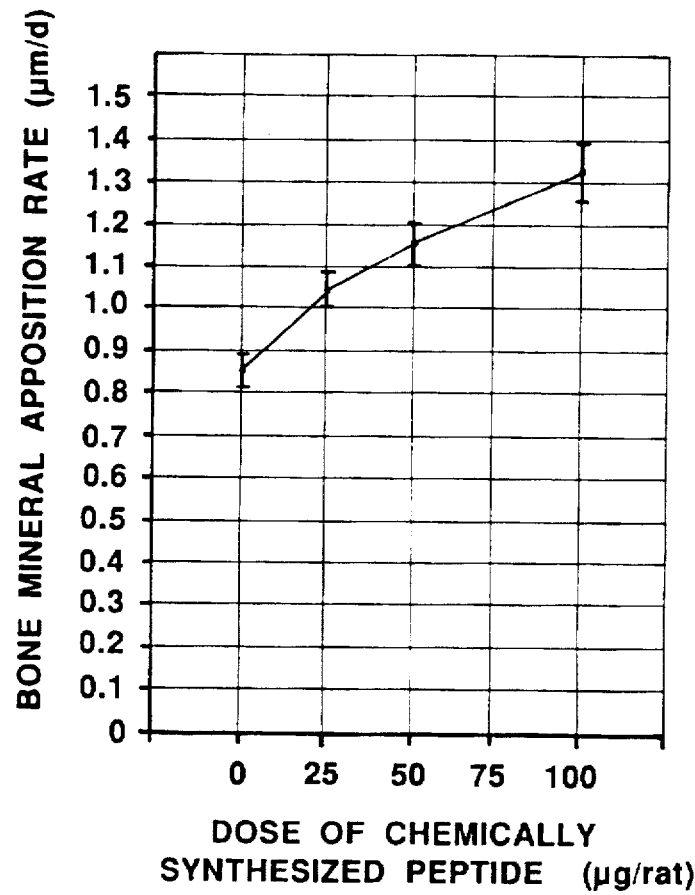

FIG. 21 graphically depicts the dose dependency of bone mineral apposition rate (µm per day) in intact rats on the amount of chemically synthesized human polypeptide (SEQ ID NO: 11) as a function of weight (µg) of polypeptide administered (N=4 for all groups).

Figure 22:
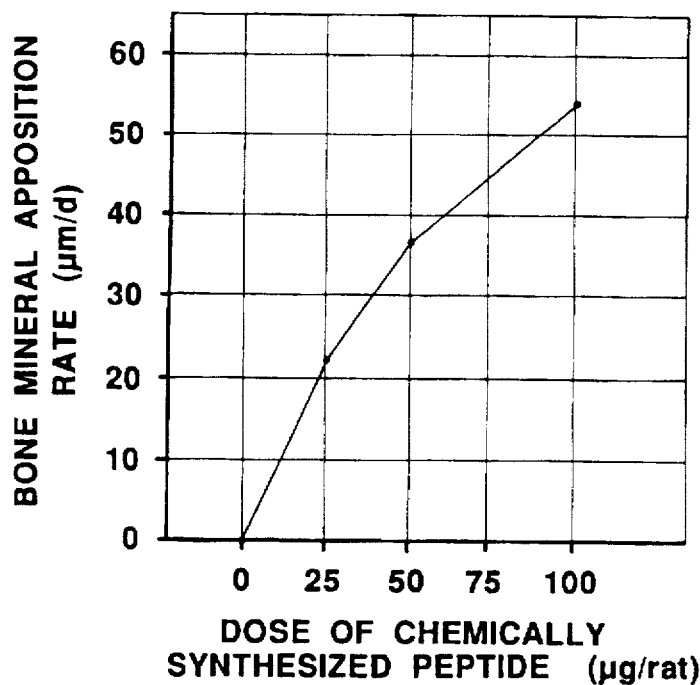

FIG. 22 graphically depicts the dose dependency of bone mineral apposition rate (percentage of change) in rats on the amount of chemically synthesized human polypeptide (SEQ ID NO: 11) as a function of weight (µg) of polypeptide administered.

Figure 23:
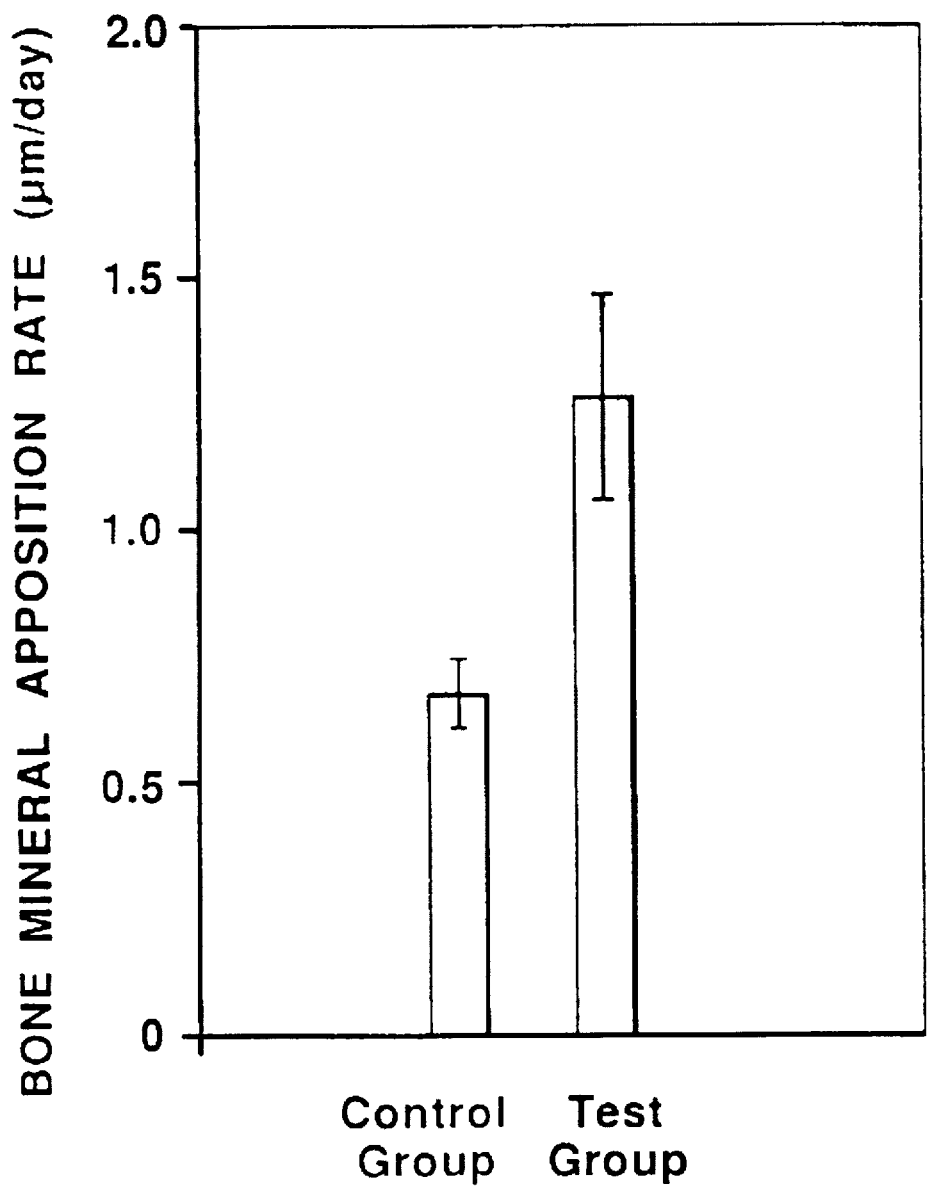

FIG. 23 graphically depicts the bone mineral apposition rate (µm per day) in rats provided with the chemically synthesized human polypeptide (SEQ ID NO: 12) through implantation. The error bars indicate±1 standard deviation (S.D.). The value of p was less than 0.001.

Figure 24:
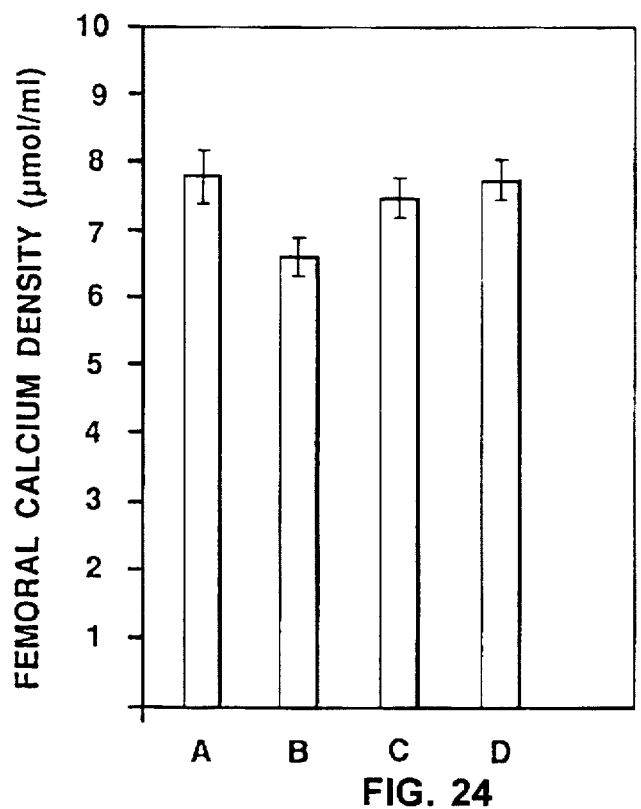

FIG. 24 graphically depicts right femoral bone calcium density of rats treated over a four week period. Group A rats were ovariectomized and injected daily with the chemically synthesized normal peptide (SEQ ID NO:11). Group B rats were ovariectomized and injected daily with control solution. Group C rats were subject to sham ovariectomization operations and injected daily with control solution. Group D were intact rats injected daily with control solution. The error bars indicate±1 standard deviation (S.D.).

Figure 25:
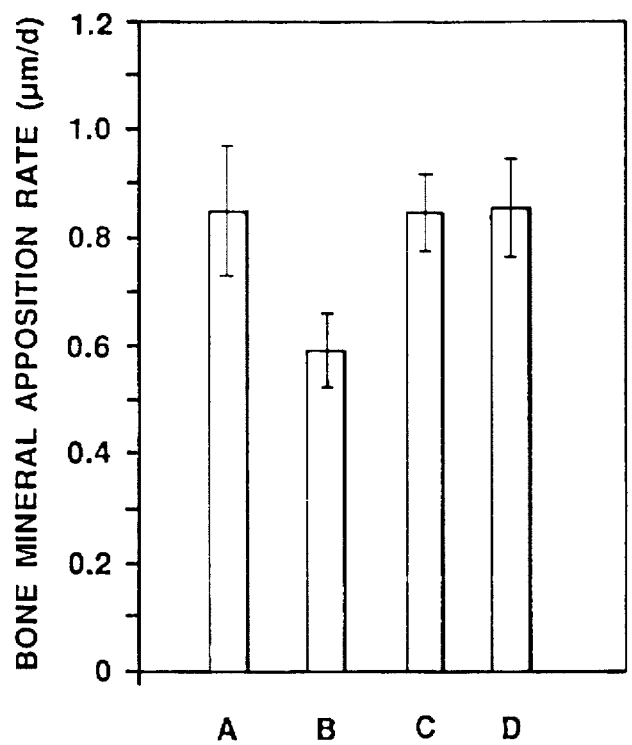

FIG. 25 graphically depicts the bone mineral apposition rate of rats as determined by tetracycline labelling after treatment as described in connection with FIG. 24. The error bars indicate±1 standard deviation (S.D.).

Figure 26:
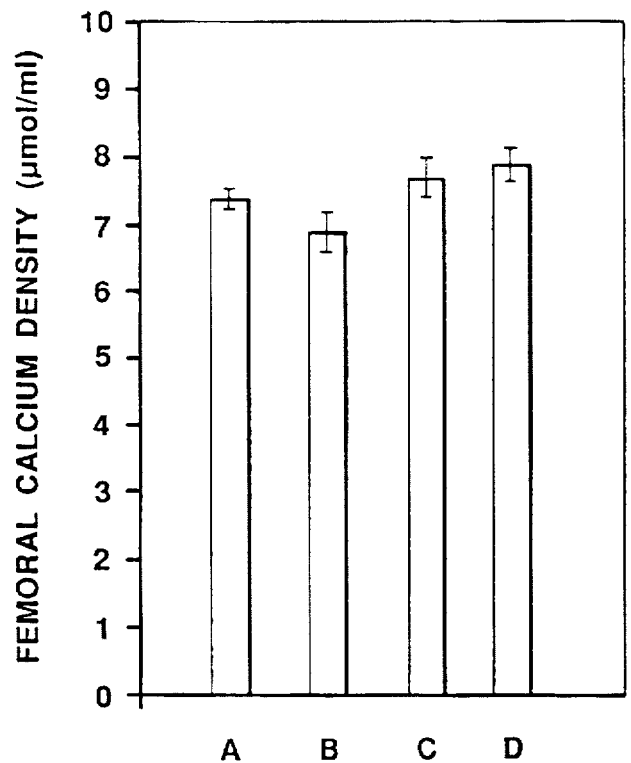

FIG. 26 graphically depicts femoral bone calcium concentration of rats treated over an eight week period. Group A rats were ovariectomized and injected daily with the chemically synthesized normal peptide (SEQ ID NO:11) beginning eight weeks after the operation. Group B rats were similarly ovariectomized and injected daily with control solution. Group C rats were subject to sham ovariectomization operations and injected daily with control solution. Group D were intact rats injected daily with control solution. The error bars indicate±1 standard deviation (S.D.).

Figure 27:
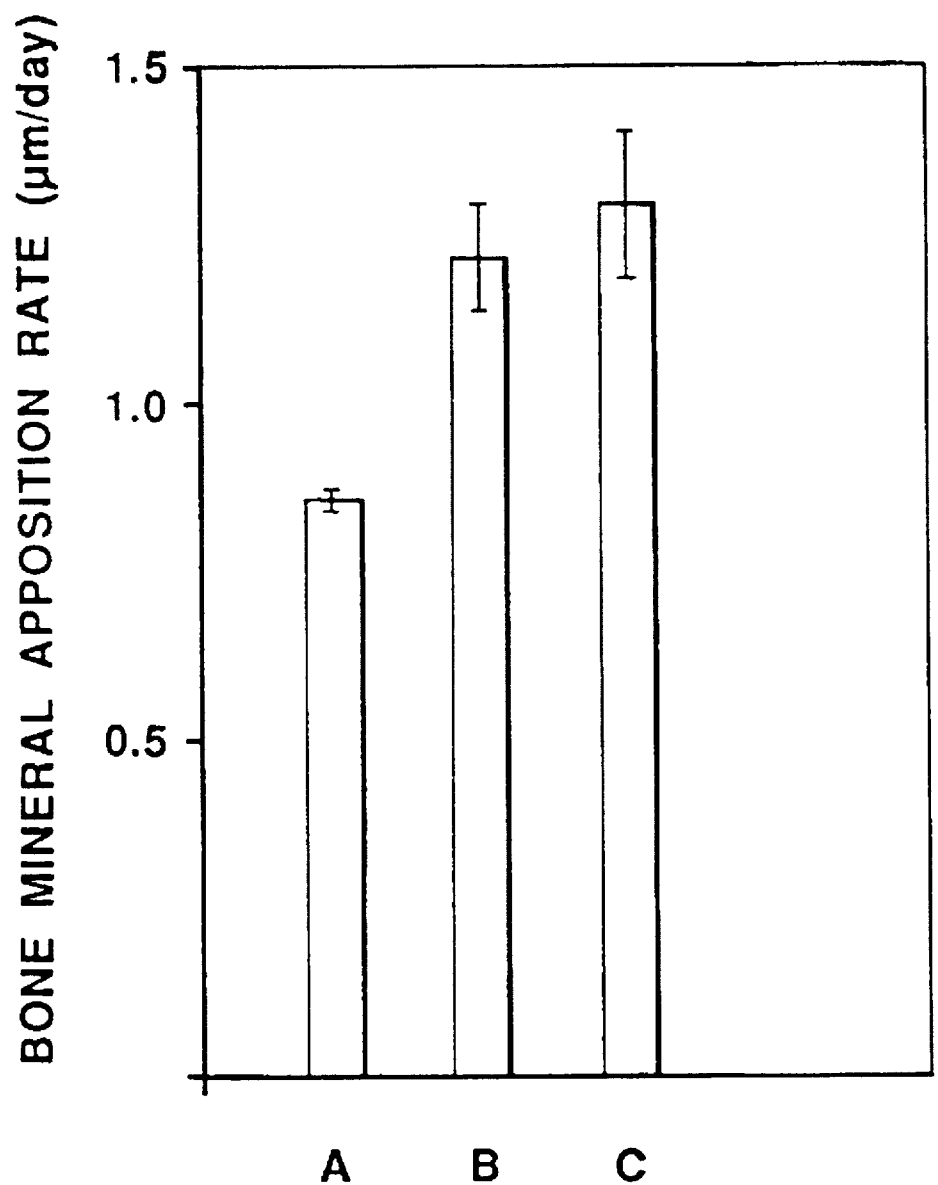

FIG. 27 graphically depicts the bone mineral apposition rate of intact rats as determined by tetracycline labelling. Group A rats were treated with rabbit antibodies to the chemically synthesized normal polypeptide (SEQ ID NO:11). Group B rats were treated with the same antibodies and the polypeptide itself. Group C is the control group. The error bars indicate ±1 standard deviation (S.D.).

Figure 28:
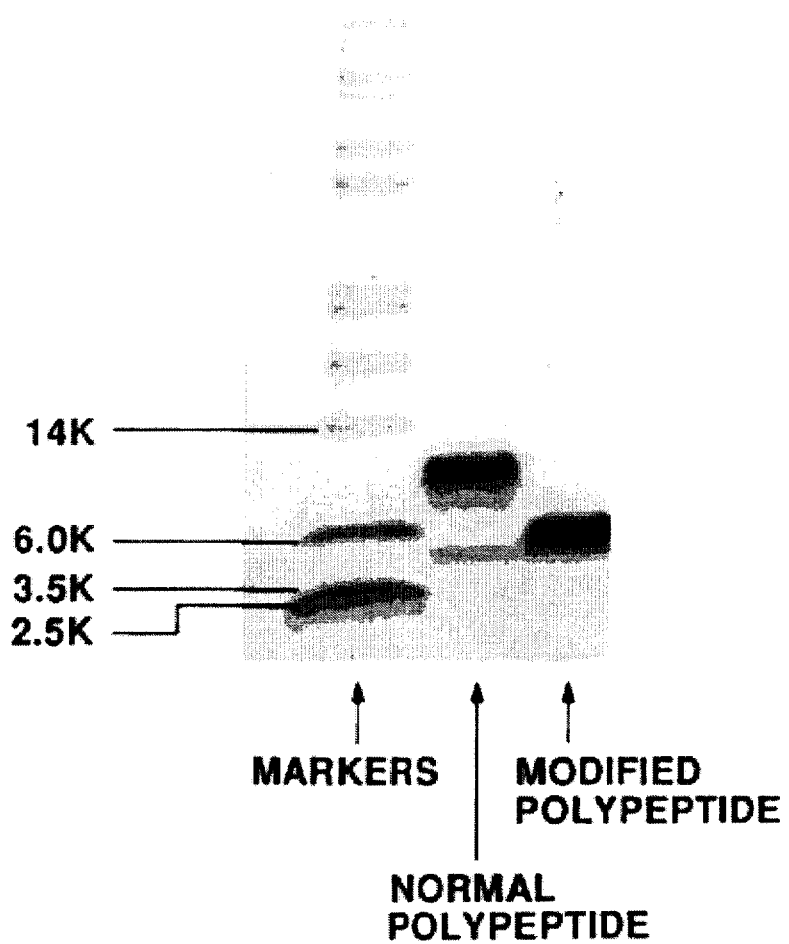

FIG. 28 shows a tricine SDS electrophoretic gel of the human chemically synthesized polypeptide (SEQ ID NO:11) and the same polypeptide containing a cys→ala substitution (SEQ ID NO:13).

Figure 29:
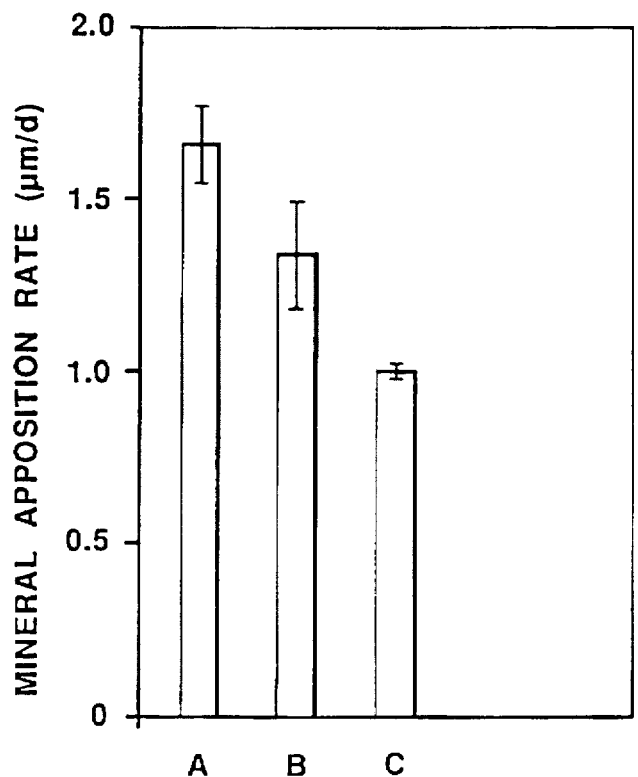

FIG. 29 graphically depicts the bone mineral apposition rate (µm per day) in rats injected with the chemically synthesized human polypeptide (SEQ ID NO:11), Group A; the modified chemically synthesized human polypeptide (SEQ ID NO:13), Group B; and control, Group C. (N=6 for all groups). The error bars indicate±1 standard deviation (S.D.).

GENERAL METHODOLOGY
INDUCTION OF HYPERPARATHYROID STATE IN RATS

Calcium deficient diet (Catalogue #113034, Lot #0186-3) used to induce the hyperparathyroid state was purchased from Dyets, 2508 Easton Avenue, Bethlehem, Pa. 18017, U.S.A. This diet contains 0.1% calcium and 0.05% phosphorus. The calcium sufficient diet (Catalogue #113035, Lot #01864) used for control animals contains 0.5% calcium and 0.05% phosphorus as specified by the manufacturer, Dyets. Both diets contains vitamin D at a concentration of 1 i.u./g. The diets are pelleted in pallets and each animal was provided with 10 pellets a day along with demineralized water. Test animals were put on these diets for a period of two weeks.

EXPERIMENTAL RATS

The Sprague-Dawley rat from Charles River Laboratory was the standard test animal. Male rats weighing between 200 to 250 g at the time of purchase were used, the rats being housed in pairs in identical cages.

TETRACYCLINE LABELLING OF BONE FOR DETERMINATION OF BONE MINERAL APPOSITION RATE IN RATS (26)

It has been demonstrated that a dose of tetracycline 24mg/kg of body weight when injected intravenously into a rat is cleared from the circulation within half an hour. That is, by such time the serum tetracycline level is not measurable by bioassay. It has also been shown that intermittent labelling doses of from 6 to 24 mg/kg b.w., result in the same measured rate of bone apposition. Thus, tetracycline given intermittently, that is, as pulse labels in this dose range appears to be a satisfactory way of labelling bone for the study of the bone mineral apposition rate.

It has also been shown, however, that in a bone forming location, the BMU, the deposition of mineralized bone matrix can be subject to interruption. Such interruption is most likely to occur when the interval between two doses of tetracycline is longer than 7 days. Such interruption is possibly due to there being more than one group of osteoblasts activated in succession over the same matrix surface location. Such osteoblast activation may be random or non-random. To avoid the influence of this phenomenon on the measurement of the rate of bone mineral deposition, 48 hour intervals between labels were used. Tetracycline hydrochloride, which has a serum half life of 8 hours when a therapeutic dose is used, was used exclusively.

Tetracycline is excited by long UV light (i.e., with a range close to the blue range) and a bright yellow fluorescence is emitted, which fluorescence is detectable in bone sections viewed with a fluorescence microscope. Tetracycline labels a bone surface when a newly formed collagen matrix begins to incorporate calcium and when such surface is sectioned, the tetracycline appears as a yellow fluorescent band. A subsequently administered dose of tetracycline appears as a second band located superficial to the first band. The distance between the two bands represent the thickness of bone matrix formed in the interval between the two doses. The rate of bone deposition can be calculated by dividing the distance with the time interval between doses. Errors can be introduced by cuts which are not perpendicular to the growing bone surface. To reduce this error, only sites in which the two bands were distinct and parallel to each other were used. Measurements made on 10 randomly chosen sites fulfilling this requirement were chosen to give readings close to the arithmetic mean of the rate.

Figure 1:
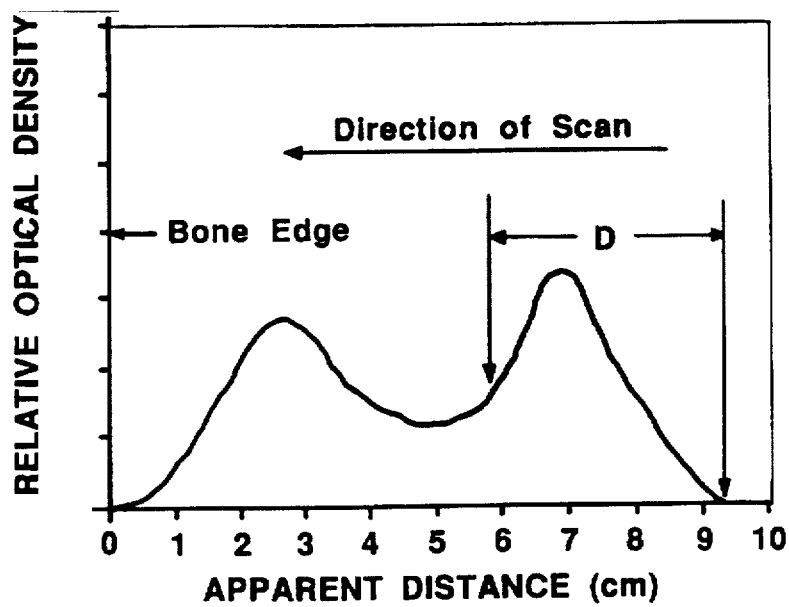
FIG. 1 is a tracing of oxytetracycline bands in a bone formation site of a rabbit given two intravenous injections of oxytetracycline spaced 48 hours apart. The vertical arrows mark the points at which the injections were given. "D" indicates the distance between these points on the tracing chart. Optical magnification ×250; mechanical magnification ×55.6. This distance can also be estimated from peak to peak.
Figure 2:
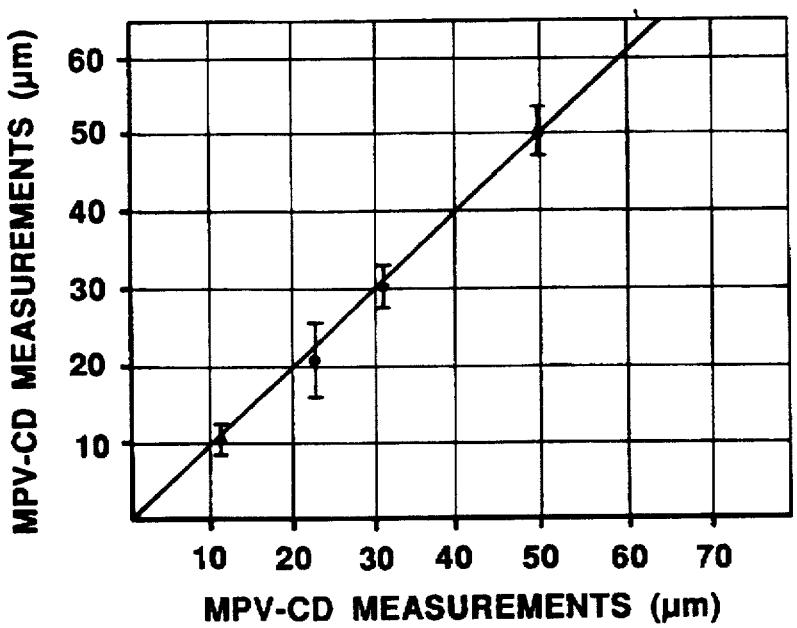
FIG. 2 is calibration of the MPV-CD Instrument for measuring the bone mineral apposition rate. A microscope grid is scanned in the equipment. The observed distances measured are plotted against the grid distances. The error bars indicate±1standard deviation (S.D.).

The measuring system used was a Leitz scanning light microscope photometer MPV-CD with a UV source being provided by a 100 W stabilized mercury burner. Sections were generally magnified using 16× objective using a moving scanning slit, the intensity of the fluorescent band was amplified and recorded. The light signal was transformed into digital output and the profile of the tetracycline intensity recorded. The distance between the intensity peaks was taken as the distance between two tetracycline bands, as shown in FIG. 1. The instrument carries a mechanical error of less than 5%. The distance measured was periodically calibrated with a microscopic grid and a good correlation was found, as shown in FIG. 2.

SKELETAL SITE FOR THE STUDY OF THE BONE MINERAL APPOSITION RATE IN RATS

The lower metaphysis of the right femur was generally chosen as the site of measurement, unless otherwise indicated. This site is located about 1 mm above the lower femoral growth plate and extends upwards towards the shaft for a distance of about 5 mm.

HISTOLOGICAL PREPARATION OF RAT BONE MATERIAL

The bone sample was dissected out of the animal after sacrifice. The bone sample was immediately fixed in a 10% aqueous solution of formaldehyde buffered to pH 7.2 by 50 mM phosphate buffer. A low pH will cause tetracycline to leach out from the bone matrix. After a 24 hour fixation period the sample was processed as follows.

| | |
|---|---|
| 80% ethanol | 24 hours |
| 95% ethanol | 24 hours |
| Absolute ethanol | 24 hours |
| Absolute ethanol | 24 hours |
| acetone | 24 hours |
| Spurr's medium: acetone, 1:1 | 24 hours |
| Spurr's medium: acetone, 1:4 | 24 hours |
| Spurr's medium | 24 hours |

The sample was then embedded in a fresh change of Spurr's medium and cured at 45° C. for 24 hours; and then cured at 80° C. for another 24 hours.

The cured block was cut into 400 μm thick sections using a Leitz saw microtome equipped with a diamond charged blade. The relatively thick sections were ground down between two ground glass plates pre-roughened with carborundum powder to a final thickness of about 10 μm, water being used as the grinding lubricant. The thin sections were dried and mounted unstained in Permount (Fisher).

PARATHYROIDECTOMIZATION OF RATS FOR ASSAYING THE EFFECT OF TEST MATERIALS ON BONE APPOSITION

Male Sprague-Dawley rats of between about 200 to 250 g. were parathyroidectomized under general nembutal anaesthesia. The parathyroid glands were destroyed by repeated freezing and thawing. One week after the surgery, the animals were anaesthetized again and 0.5 ml of blood taken from the tail vein. The animal was then deprived of food overnight. The next morning, the animal was again anaesthetized and 0.5 ml of blood taken from the tail vein. The serum calcium before and after fasting was measured. A fall of the serum calcium in the fasting state to 1.8 mM or lower was taken as an indication of successful surgery. The test material was then injected into the tail vein followed by the first dose of tetracycline or injected intramuscularly. The second tetracycline label was given 48 hours later and the animal killed 24 hours thereafter by carbon dioxide narcosis. The bone sample was then taken for bone mineral apposition rate measurement.

INITIAL SCREENING OF RAT SERUM PROTEINS AND PEPTIDES BY GEL PERMEATION

The range of molecular weights of proteins and peptides in the serum is wide and the number of proteins and peptides circulating in the blood is very large. Gel permeation was used to initially classify the serum protein components by certain ranges of molecular size, and to test the biological effect of these classes on the apposition of mineralized bone matrix.

MATERIALS AND METHODS

A Pharmacia glass column, 2.5 cm in internal diameter and 90 cm long was used. Sephadex G 50 from Sigma, which provides a medium fine grain matrix was used. Dried Sephadex matrix (25 g) was poured into a 1000 ml conical flask and 800 ml of deionized water containing 0.02% $NaN_3$ was added to swell the dry matrix. This was left overnight at room temperature for thorough swelling of the matrix.

Following the swelling of the Sephadex matrix, a packing reservoir was connected to the upper end of the column and the swollen matrix allowed to settle into the column for about three hours. The reservoir was then removed, the upper fitting of the column installed and the column equilibrated with a buffer consisting of 20 mM Tris.Cl pH 7.2 and 50 mM NaCl. The buffer was delivered by a metered peristaltic pump (Pharmacia) at a rate of 2.5 ml per min. During this procedure, the matrix was found to further settle down in the column and it was necessary to refill the column with matrix periodically until totally filled. The column was then further equilibrated with the same buffer for another three hours at 4° C.

The Sephadex G 50 column was calibrated with molecular markers consisting of the following:

| Human IgG | M. W. 150,000 | 6.00 mg |
| BSA | M. W. 66,000 | 10.00 mg |
| Ovalbumin | M. W. 45,000 | 8.25 mg |
| Cytochrome C | M. W. 12,400 | 4.00 mg |

These were obtained from Sigma and dissolved in 2 ml of deionized water for loading. The molecular markers were loaded and run with the calibrating buffer at a rate of 2.5 ml per min. and 50 fractions of ten ml were collected. The absorption of UV at 280 nm by individual fractions was measured by a Varian UV/VIS spectrophotometer.

Forty male Sprague-Dawley rats with weight between 173 to 212 g on arrival in the laboratory were used. Four of these rats became ill during the experiment (diagnosed as having respiratory infections) and they were eliminated. The 36 remaining rats were divided into test and control groups of 18 rats per group. The rats of the test group were given the calcium deficient diet and those of the control group the calcium sufficient diet, described above. All the rats were then sacrificed and the serum collected and pooled. Calcium and phosphorus concentrations in the pooled serum were measured using calorimetric methods and kits purchased from Worthington.

PREPARATION OF RAT SERUM FOR GEL PERMEATION

Postmortem blood samples taken from individual rats were centrifuged at 2,000 rpm for 15 minutes in a Beckman J6B centrifuge using the JS 4.2 rotor. The serum from rats of the same group was pooled together. PMSF (Sigma) and dithiothreitol (Biorad) were added to a concentration of 1 mM respectively. The serum was then stored frozen at $-85°$ C. For gel permeation, the frozen serum was thawed and centrifuged in a Beckman J2-21 centrifuge at 12,000 g for 30 minutes using a JA 17 rotor to rid the sample of particulate materials and lipid.

GEL PERMEATION CHROMATOGRAPHY OF TREATED RAT SERUM

Ten ml of serum was loaded and chromatographed with the same buffer used for equilibration. Before loading, the column was equilibrated for three hours with the buffer and the sample then run at a flow rate of 2.5 ml per minute with the eluent collected in 10 ml fractions.

The collected fractions were pooled according to molecular weight then dialyzed in 1000 ml of 20 mM Tris.Cl pH 7.2 containing 1 mM of each of PMSF and DTT using a 2.5 cm wide Spectrophor dialysis bag with MWCO 3500. The dialysis was carried out over 24 hours at 4° C. with three changes of dialysis buffer. The dialysed samples were then lyophilized in a Virtus lyophilizer, and stored at $-20°$ C.

TEST OF BIOLOGICAL ACTIVITY OF SERUM FRACTIONS

There is some difficulty in comparing activities among fractions according to weight because of the variation in concentrations of components in the fractions. Arbitrarily, respective fractions from two rats were administered to one test animal. The dose was dissolved in 0.5 ml of 20 mM Tris.Cl pH 7.2 and 50 mM NaCl and injected intramuscularly into a PTX test animal. This was followed immediately by an intravenous dose of tetracycline hydrochloride in the manner described above. After 24 hours, another intravenous dose of tetracycline was given and 24 hours later, the rat killed and the bone mineral apposition rate estimated as stated above.

INITIAL RESULTS INVOLVING ISOLATION OF RAT POLYPEPTIDES

Figure 3:
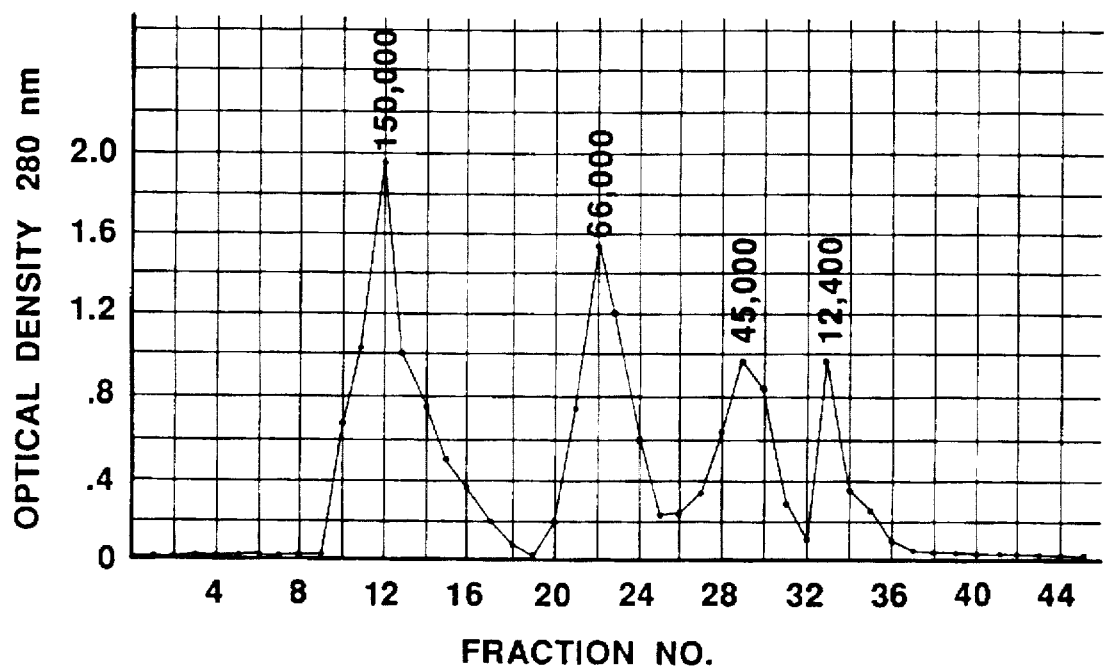
FIG. 3 is calibration of the Sephadex G50 column. The column is 2.5 cm in the internal diameter and 90 cm long. The mobile phase was 20 mM Tris.Cl (pH 7.2) and 50 mM NaCl with a flow rate of 2.5 ml/min. The molecular weight standards used were human IgG (MW 150K), bovine serum albumin (MW 66K), ovalbumin (45K) and cytochrome C (12.4K). The elements were collected as 10 ml fractions. The O.D. 280 absorptions of individual fractions are shown.

The molecular marker elution profile is shown in FIG. 3 and Table One.

TABLE ONE

Molecular Marker Elution Profile in Gel Permeation

| Molecular Weight | Elution Volume |
| --- | --- |
| >150,000 | 100 ml |
| 150,000–66,000 | 100 ml |
| 66,000–45,000 | 70 ml |
| 45,000–12,400 | 40 ml |
| <12,000 | 100 ml |

No unquestionable difference between the calcium and phosphorus concentrations in serum from rats on a calcium deficient diet and rats on a calcium sufficient diet was found although the calcium concentration appears to be lower for the former (2.55 mM compared to 2.85 mM for serum of rats on calcium sufficient diet). The phosphorus concentration was 0.33 mM for the former and 0.43 mM for the latter. These differences may be the result of compensatory secondary hyperparathyroidism in the rat on calcium deficient diet. However, this was not confirmed with a PTH assay in the rat on calcium deficient diet.

Serum fractions from the control and test rats were pooled according to the molecular weight ranges indicated in Table One.

Figure 4:
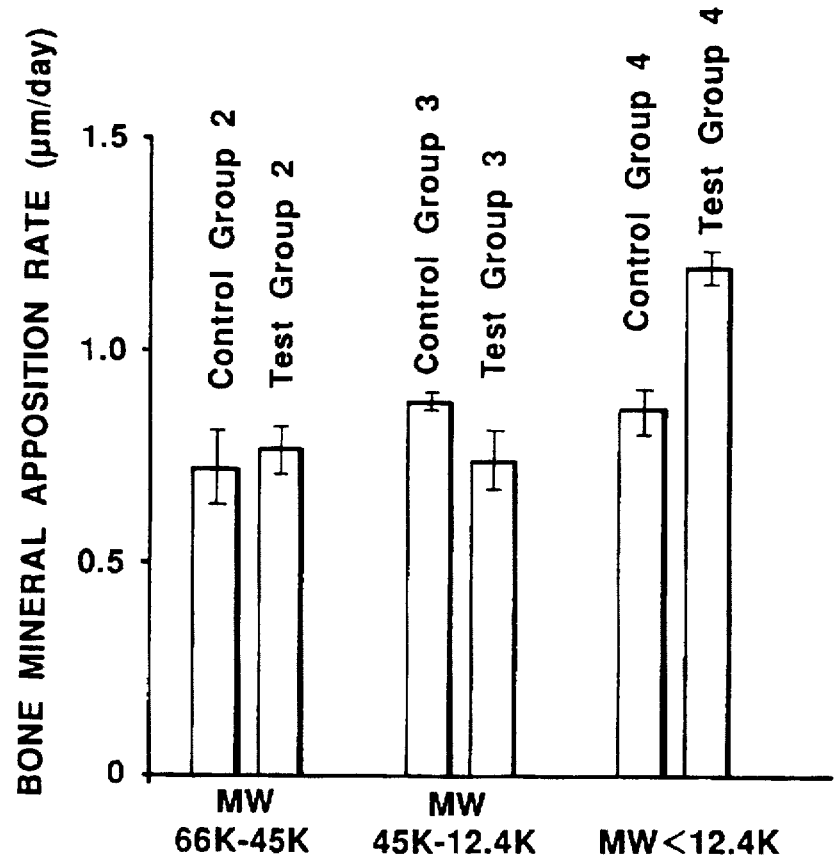
FIG. 4 shows the effect of certain serum components on bone formation. The rate of bone formation is measured by tetracycline labelling, details of the method being described in the text. The serum from rats on either a calcium sufficient diet (0.5% calcium) or a calcium deficient diet (0.1% calcium) is fractioned according to the molecular weight sized by gel permeation. The fractions tested are with molecular weight between 66K and 45K (Number of rats in control group=3; Number of rats in test group=4), between 45K and 12.4K (N=4 for control group; N=4 for test group), and under 12.4K (N=4 for each group). Fractions of serum from two rats were tested in one 250–300 g parathyroidectomized rat. There are 3 control and 3 test groups. The test group receiving the serum fraction with molecular weight below 12.4K showed a higher bone mineral apposition rate than its corresponding control group (P<0.05). The error bars indicate±1 standard error (S.E.).
Figure 5A:
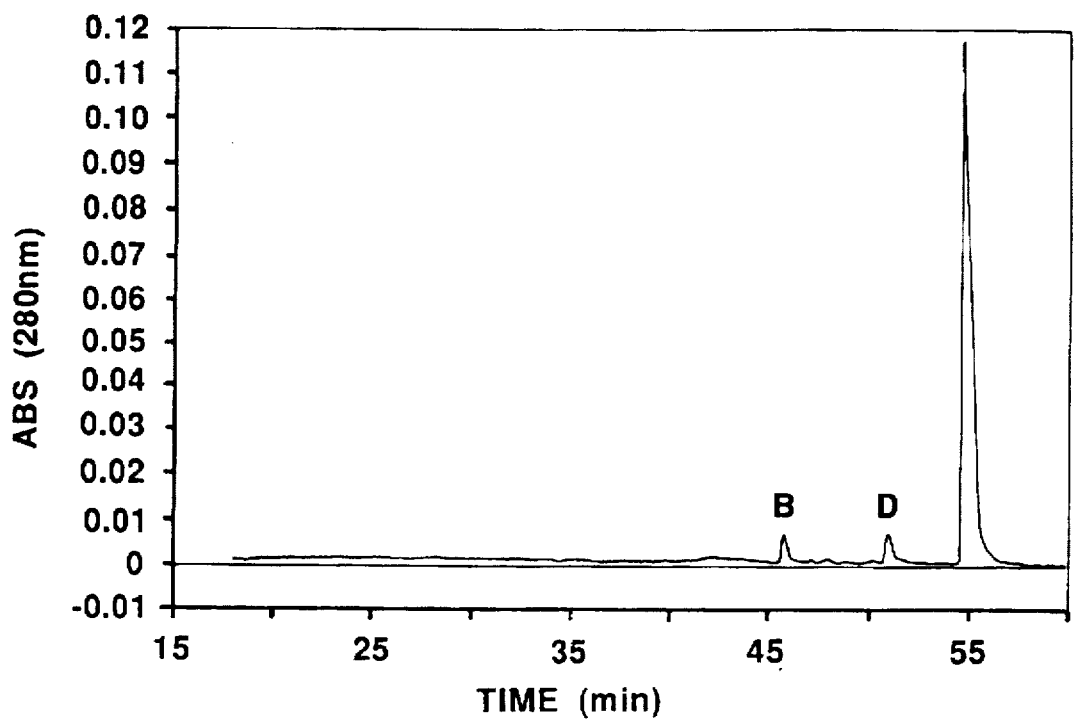
FIG. 5A shows absorbance at 280 nm of sized fractions with MW<12.4K from calcium deficient rats that were chromatographed with C18 reverse phase HPLC, as a function of time (minutes). Peaks B and D were tested for bone stimulatory activity on parathyroidectomized rats.
Figure 5B:
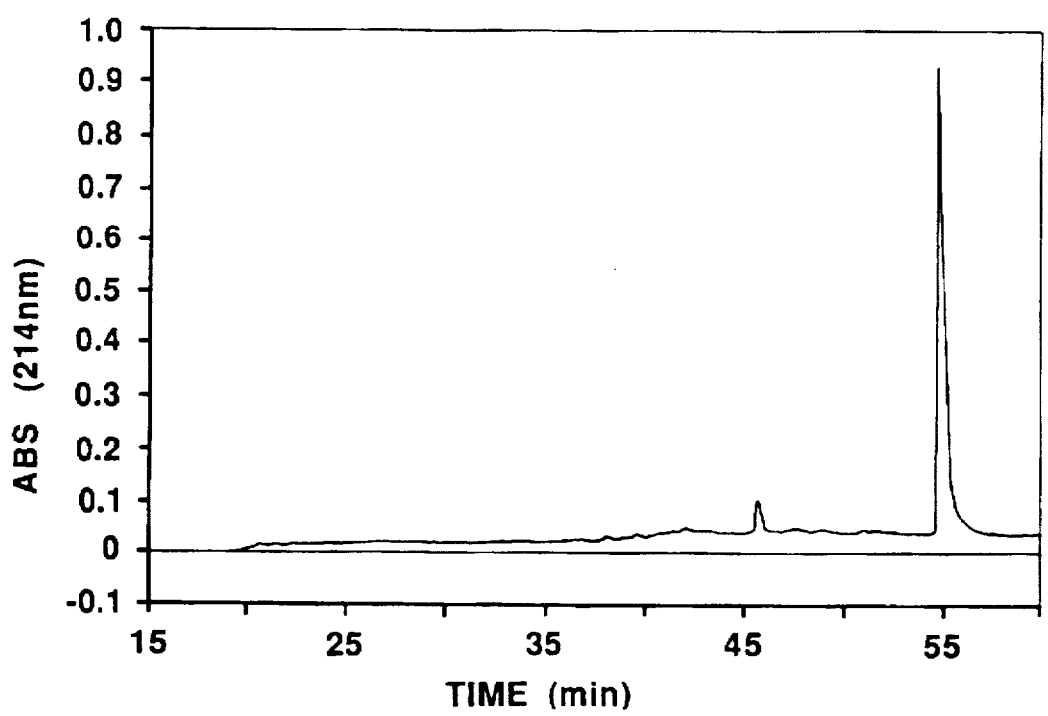
FIG. 5B shows absorbance at 214 nm sized fractions with MW<12.4K from calcium deficient rats that were chromatographed with 18 reverse phase HPLC, as a function of time (minutes).
Figure 6:
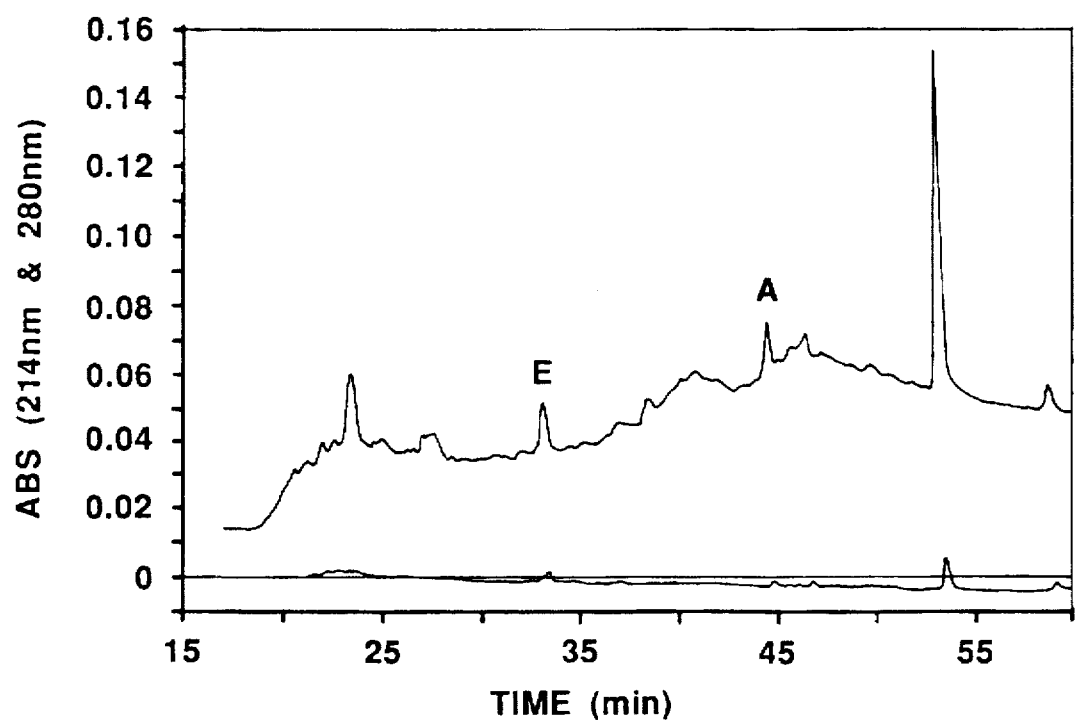
FIG. 6 shows absorbance at 214 nm (upper tracing) and 280 nm (lower tracing) of sized fractions with MW<12.4K from calcium deficient rats that were chromatographed with C18 reverse phase HPLC, as function of time (minutes). Peaks A and E were tested for bone stimulatory activity on parathyroidectomized rats.
Figure 7:
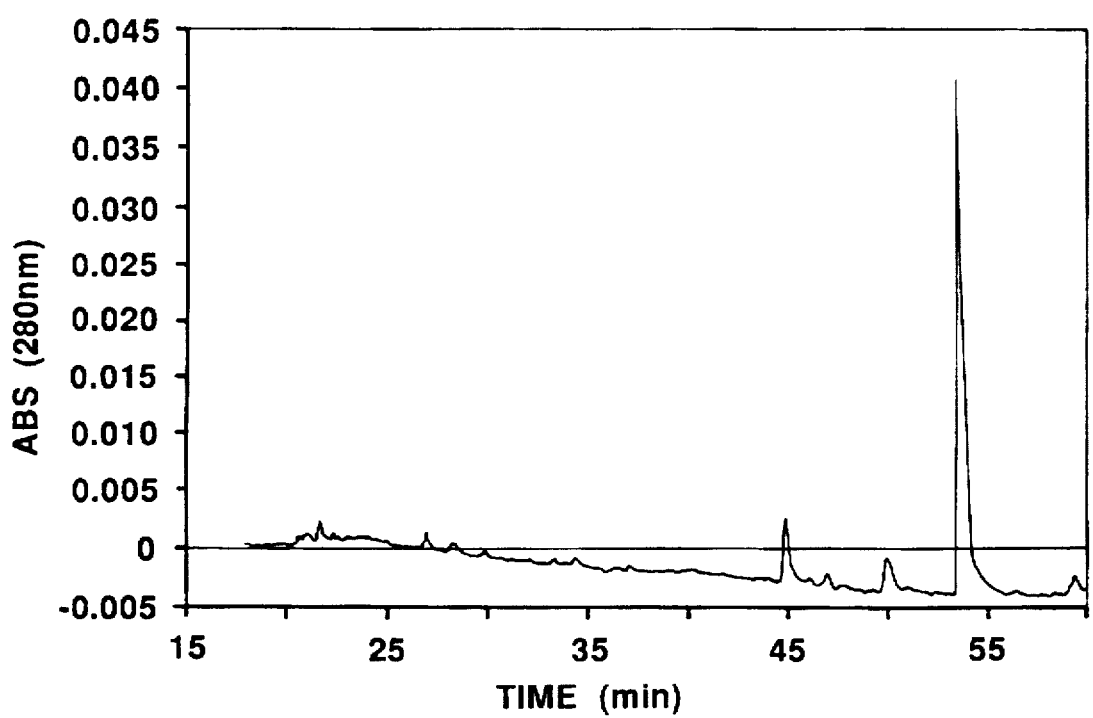
FIG. 7 shows absorbance of 280 nm of sized fractions with MW<12.4K from calcium deficient rats that were chromatographed with C18 reverse phase HPLC, as function of time (minutes).
Figure 7A:
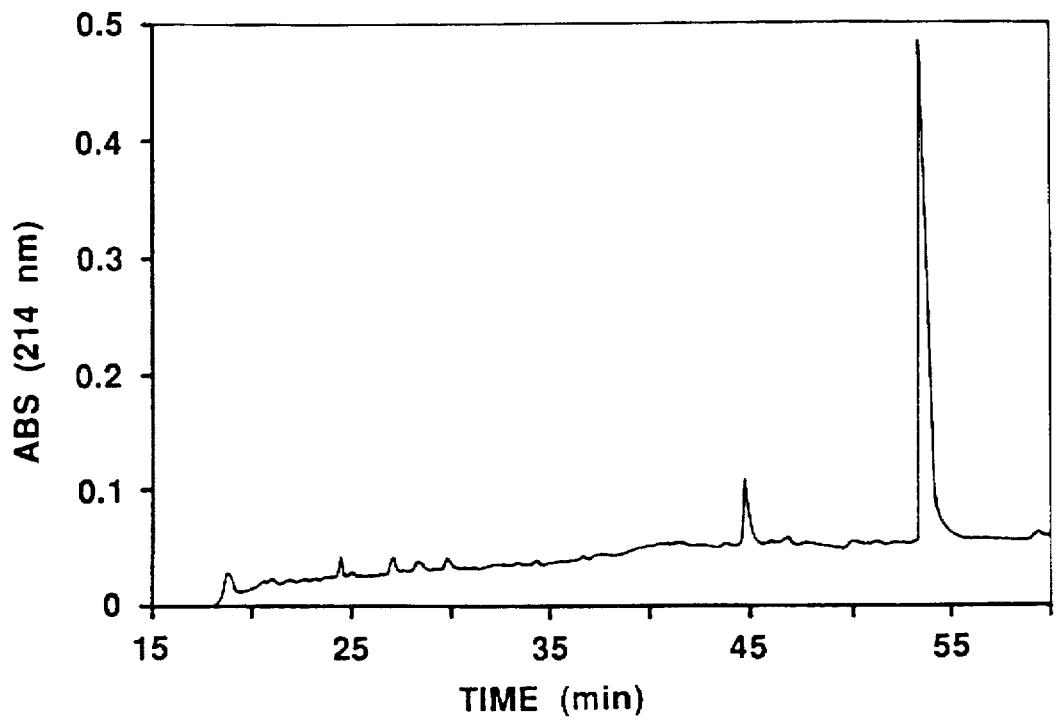
FIG. 7A shows absorbance at 214 nm of sized fractions with MW<12.4K from calcium deficient rats that were chromatographed with C18 reverse phase HPLC, as function of time (minutes).
Figure 8:
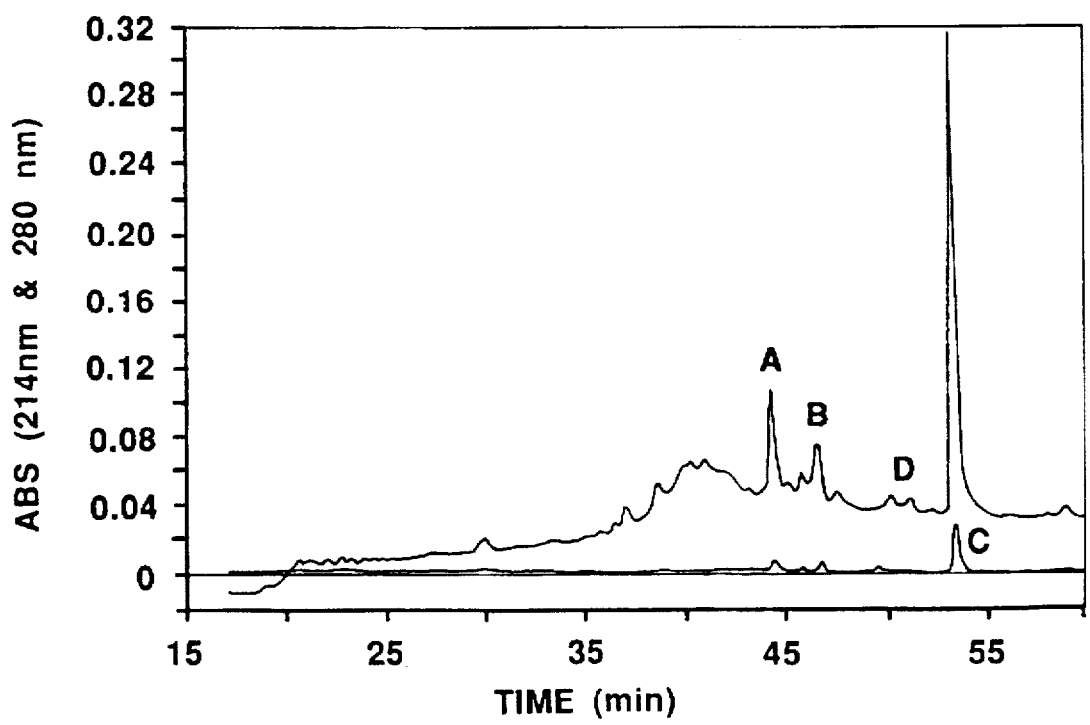
FIG. 8 shows absorbance at 214 nm (upper tracing) and 280 nm (lower tracing) of sized fractions with MW<12.4K from calcium deficient rats that were chromatographed with C18 reverse phase HPLC, as a function of time (minutes). Peaks A, B, C and D were tested for bone stimulatory activity on parathyroidectomized rats.
Figure 9:
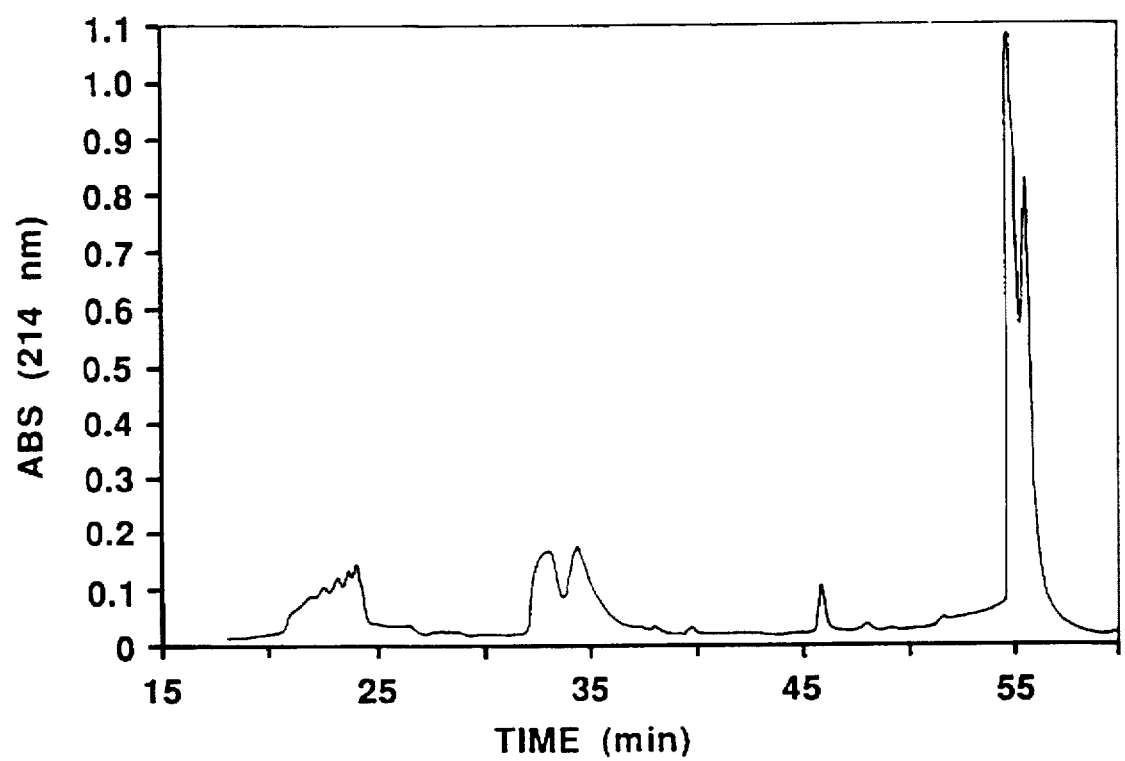
FIG. 9 is a control run for experiments illustrated in FIGS. 5A to 8, showing absorbance at 214 nm, using serum from normal rats, of sized fractions with MW<12.4K that were chromatographed with C18 reverse phase HPLC, as a function of time (minutes).

Out of 40 rats subject to parathyroidectomy, only 25 survived the operation. The serum Ca of non-fasting state for these 25 rats was 2.57±S.D. 0.05 mM and that of the fasting state was 1.70±S.D. 0.04 mM. It was concluded that the operation was successful in these animals. The fractions with molecular weight larger than 150,000 and between 150,000 and 66,000 were not tested as the amount of protein present was too great to be administered in a single dose without ill effect on the animal. Therefore, there were only three fractions tested for the calcium sufficient serum and the calcium deficient serum. For each fraction, 4 animals were used. One rat receiving the fraction from the calcium sufficient serum with molecular weight between 66,000 and 45,000 died during anaesthesia when the intravenous tetracycline was given. The results are shown in FIG. 4.

A statistically significant difference between the bone mineral apposition of the rat receiving calcium sufficient fraction with molecular weight less than 14,500 and the rats receiving the corresponding fraction from the calcium deficient serum (P<0.05) was found.

These preliminary results indicated that the serum fraction containing molecular weight components of less than 14,500 may have a stimulant effect on the rate of apposition of mineralized bone matrix.

EXPERIMENTS INVOLVING LOW MOLECULAR WEIGHT SERUM COMPONENTS OBTAINED FROM CALCIUM DEFICIENT RAT SERUM

MATERIALS AND METHODS

Fifty male Sprague-Dawley rats, each weighing between 200 and 250 g, were used. Half of the rats were given a calcium deficient diet and half a calcium sufficient diet. These rats were sacrificed by carbon dioxide narcosis after being on the special diets for 2 weeks. The post mortem blood was taken through cardiac puncture into a serum vacuum tube immediately after death. Serum was collected by centrifugation in a Beckman J6B centrifuge at 2,000 rpm for 20 minutes at 4° C. The serum samples were then pooled according to test serum (calcium deficient) and control serum (calcium sufficient) and 100 µl was taken for the estimation of calcium and phosphorus concentrations. PMSF (phenylmethyl sulfonyl fluoride) and DTT (dithiothreitol) were added to a concentration of 1 mM respectively. The serum was then frozen at −85° C.

RAT SERUM FRACTIONATION PROCEDURE: GEL PERMEATION FOLLOWED BY REVERSE PHASE HPLC

Initial gel permeation with a Sephadex G 50 column was carried out as described above. The fraction with molecular weight<14,500 was collected, dialyzed and lyophilized as before.

The lyophilized material was dissolved in 5 ml of buffer consisting of 25 mM Tris.Cl pH 7.5; 150 mM NaCl; 1 mM PMSF; and 1 mM DTT. Some materials were found not to be soluble and were pelleted down by centrifugation in a Beckman J2-21 centrifuge at 12,000 g, using a JA 17 rotor, and discarded. 800 µl of the dissolved material was taken for protein determination.

Accordingly, 0.5 mg of material in 1 ml of the above buffer was filtered through a Hewlett Packer sample filter before loading. The column used was a preparative C18 column from Beckman, 2.12×150 cm. The solvent delivery system was a Beckman Gradient Solvent delivery system Model 126 with a Beckman UV detector Model 167. The data were analyzed using Beckman System Gold software. The sample was injected manually through a Valco injector and eluted at a flow rate of 2 ml per min. The gradient was set up as follows:

Solvent A: Water with 0.1 % Trifluoroacetic Acid
Solvent B: 95% Acetonitrile in Water with 0.1 % Trifluoroacetic Acid

| Program: | | |
|---|---|---|
| 0–5' | 100% A | 0% |
| 5–75' | 40% A | 60% B |
| 75–80' | 100% A | 0% B |
| 80' | End | |

Fractions were collected every 0.5 minute in a Gilson fraction collector Model 202 and corresponding peaks of the four runs pooled and lyophilized.

The calcium concentration of the pooled test serum was found to be 2.50 mM and for the pooled control serum, 2.87 mM. The phosphorus concentration was 0.35 mM for the test serum and 0.45 mM for the control serum. The protein concentrations of the redissolved lyophilized material were 1.2 mg per ml for the test sample and 1.5 mg per ml for the control sample. The elution profiles for the test and control materials are shown in FIGS. 5 to 9. Some difference was found between the elution profiles among runs for the test serum and control serum. In the test material, there was a distinct peak eluted just before 55 minutes in 3 out of the 4 runs. For the control, there were two peaks coming just after 55 minutes.

TEST OF FRACTIONS OBTAINED FROM THE SERUM OF RATS ON A CALCIUM DEFICIENT SERUM ON BONE APPOSITION RATE

MATERIALS AND METHODS

Biological tests on the effect of different fractions on the apposition rate of mineralized bone were performed on the test serum only, the aim of these experiments being to find one component having biological activity. Corresponding peaks from the 4 runs were thus pooled and dissolved in 2.5 ml. of 10 mM tris.Cl pH 7.2 and 50 mM NaCl. A volume of 0.8 ml of the material was used for testing, the remaining material being frozen for future use.

Ten Sprague-Dawley rats were parathyroidectomized and 0.4 ml of the material from each peak was injected into each test animal. Two animals were used for each of the five peaks collected, labelled A to E in FIGS. 5A to 8. The bone mineral apposition rate was estimated by tetracycline labelling according to the method already described.

Figure 10:
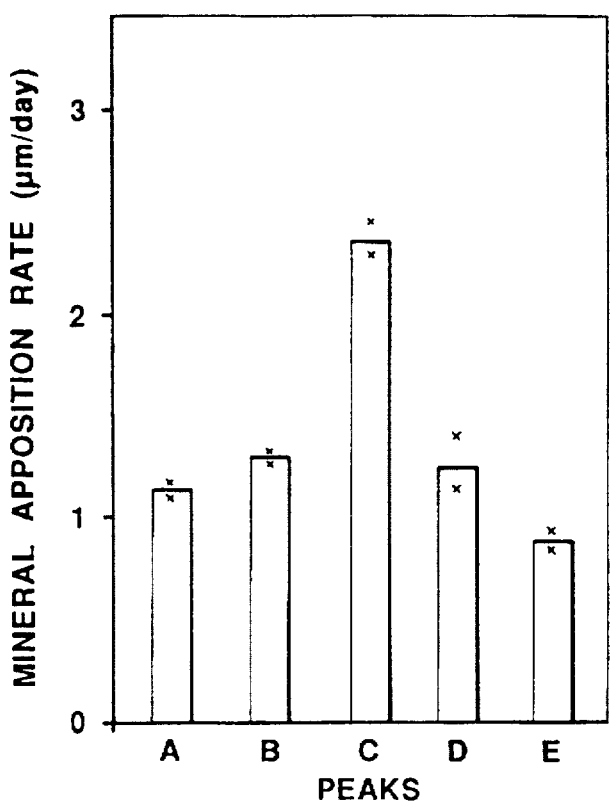
FIG. 10 shows biological activities of materials eluted from a C18 column. The pooled peaks were lyophilized and redissolved in 2.5 ml of buffer. Of this, 0.4 ml was injected into a parathyroidectomized test animal. Two animals were used for an individual peak. The "x" indicates the rate of the individual test animal and the histogram represents the mean. Because of the small animal number, no statistical analysis was done.

Of the five peaks tested, peaks A, B, D and E displayed about the same effect on the bone mineral apposition rate while peak C appeared to cause a higher rate than the other groups. See FIG. 10.

DOSE DEPENDENCY OF BONE MINERAL APPOSITION RATE ON A PARTICULAR FRACTION ISOLATED FROM RAT SERUM BY REVERSE PHASE HPLC

Material from Peak C (1.7 ml) was thawed and 400 µl taken and diluted to 800 µl for determination of protein concentration by the Belford method. The remaining portion was adjusted with the same solubilizing buffer to a concentration of 3 µg per 100 µl and nine rats were parathyroidectomized, their non-fasting and fasting serum calcium concentrations indicating successful operations. Three rats received 6 µg of the test material from peak C in volumes of 200 µl by intravenous injection. Three rats received 3 µg of the material with the injection volume adjusted to 200 µl with the solubilizing buffer. Three rats received 200 µl of the solubilizing buffer as control. The bone mineral apposition rate was determined as previously described.

Figure 11:
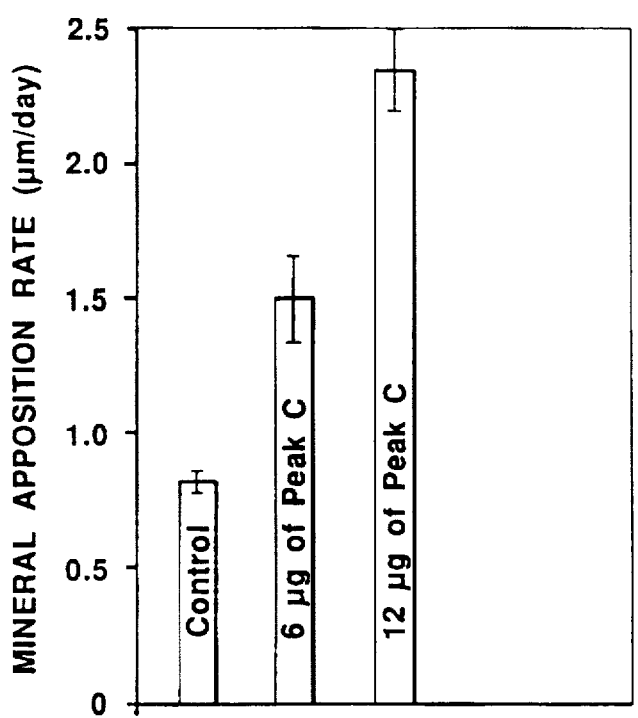
FIG. 11 shows dose dependency effect of material in peak "C" on bone formation. The polypeptide concentrations were determined by Belford Reagent. In a first group of three rats (middle bar of graph) 6 µg per rat was used and in a second group of three rats (last bar) 12 µg per rat for the other. The control group of three rats (first bar) received the carrier buffer. The animals used were pre-parathyroidectomized. There is a dose dependent response (P<0.05). The error bars indicate±1 standard error (S.E.).

The rate of apposition of control rats was found to be 0.81 µm/day (S.D.=0.09); for the rats receiving 3 µg of peak C, 1.51 µm/day (S.D.=0.23); and for rats receiving 6 µg of peak C, 2.36 µm/day (S.D.=0.25), there being a significant difference among groups ($P<0.05$). See FIG. 11.

It was thus demonstrated that a class of protein or peptide found in the serum of rats having a calcium deficient diet for two weeks is capable of stimulating the apposition of mineral bone in the rat. This effect is dose dependent up to 6 µg per approximately 300 g rat.

ELECTROPHORETIC FRACTIONATION OF THE LOW MOLECULAR WEIGHT FRACTION OF SERUM FROM RATS ON CALCIUM DEFICIENT DIETS

Serum components having molecular weights less than 30,000 were separated by molecular weight polyacrylamide gel electrophoresis.

MATERIALS AND METHODS

Twenty male Sprague-Dawley rats were given the calcium deficient diet for three weeks. Their weight on arrival was between 209 and 245 g. After two weeks on the diet, their weight was between 248 and 302 g. The rats were then sacrificed by carbon dioxide narcosis and postmortem blood was taken by cardiac puncture. The serum samples were collected and pooled as described above. The serum calcium was found to be 2.56 mM and phosphate 0.33 mM. The total volume of serum was 92 ml. PMSF and DTT were added to 1 mM respectively. The serum was then centrifuged at 12,000 g. for 30 minutes in Beckman J2-21 centrifuge, using JA 17 rotor.

The fraction with molecular weight between 3,000 and 30,000 was collected and concentrated by ultrafiltration. The serum was first ultrafiltrated in an Amicon 50 ml concentrator with a YM 30 membrane, the molecular cut off point is 30,000. The filtrate was collected. When the retained volume went down from the original 92 ml to 10 ml, 40 ml of buffer consisting of 10 mM Tris.Cl pH 7.2, 50 mM NaCl, 1 mM PMSF, and 1mM DTT were added and the ultrafiltration was carried out further until the retained volume went down again to 10 ml. This second filtrate was pooled with the first and the final retained volume was discarded.

The pooled filtrate was further ultrafiltrated with the same unit using YM 3 membrane with molecular cut off point of 3,000. The filtrate this time was discarded and the retained volume saved. When the retained volume went down to 10 ml, 40 ml of the same buffer were added and the ultrafiltration continued. This procedure was repeated once. As the final retained volume went down to 10 ml, it was transferred to another Amicon concentrator with 10 ml capacity, and further concentrated to a final volume of 1 ml. The ultrafiltration was carried out under 55 psi of prepurified nitrogen at 4° C.

ACRYLAMIDE GEL ELECTROPHORESIS

A Hoeffer Mighty Small vertical gel apparatus was used. A 0.75 mm thick 15% phosphate gel was cast and run as follows:

| | | |
|---|---|---|
| Resolving gel | 30% acrylamide (19:1) | 15 ml |
| | 1 M Tris.phosphate pH 6.9 | 3 ml |
| | 10% SDS | 0.3 ml |
| | 10% ammonium persulphate | 150 µl |
| | TEMED | 50 µl |
| | Water to | 30 ml |
| Stacking gel | 30% acrylamide (19:1) | 2.3 ml |
| | 1 M Tris.phosphate pH 6.9 | 1 ml |
| | 10% SDS | 0.1 ml |
| | 10% ammonium persulphate | 50 µl |
| | TEMED | 30 µl |
| | Water to | 10 ml |
| Running buffer | 1M Tris.phosphate pH 6.9 | 15 ml |
| | 10% SDS | 3 ml |
| | Water to | 300 ml |

The gel was pre-run at a constant voltage of 100 V for 30 minutes. Samples were run at a constant voltage of 100 V for 2 hours. Water at 20° C. was circulated through the cooling device of the apparatus.

The protein concentration was estimated by the Belford method. Tris.phosphate pH 6.9 and SDS were added to the sample to a final concentration equal to those in the running buffer. The protein concentration was adjusted to 100 µg per 15 µl. The total volume of sample was 1.65 ml. The sample was incubated for 30 minutes at 60° C. before loading.

Low molecular weight marker from BDH was treated in the same way as the sample. The concentration was adjusted to 1 µg of individual markers per 12 ml. 15 µl of sample and marker were loaded into 0.5 cm wide wells.

Figure 12:
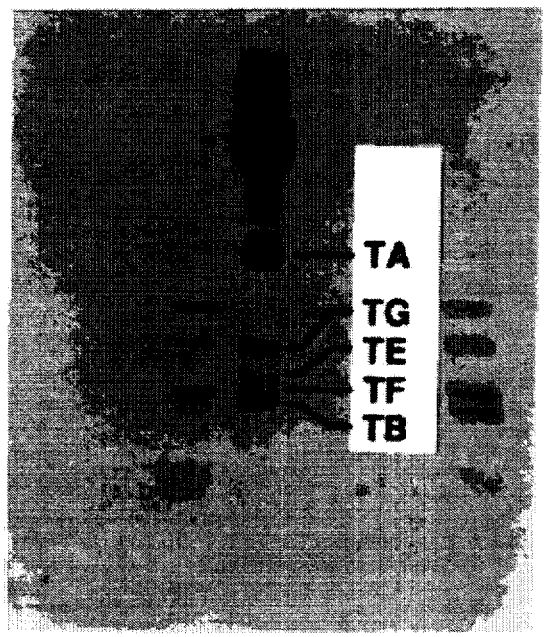
FIG. 12 shows an acrylamide gel electrophoresis of a calcium deficient rat serum fraction with molecular weights between 30–3K. The calcium deficient serum was subject to ultrafiltration with MWCO (molecular weight cut off) membranes of 30K and 3K to obtain the fraction with MW between 30K and 3K. 100 µg of the fraction determined by Belford Reagent was loaded onto 15% phosphate acrylamide gel. The gel was cast with 100 mM of Tris.phosphate, pH 6.9 with 0.1% SDS. The sample was treated with 100 mM Tris.phosphate, pH 6.9, and 0.1% SDS at 60° C. for 30 minutes without reducing agent. The sample was then loaded and run at constant voltage of 100 V (about 8 V/cm) for 2 hours and then stained with comassie blue. Five low molecular weight bands were identified and labelled as TA,TB,TE,TF,TG.

The results of the phosphate gel electrophoresis are shown in FIG. 12. There are one huge and several small higher molecular weight bands. Several low molecular weight bands are also present and they are labelled as TA, to TE.

BIOLOGICAL ACTIVITIES OF RAT SERUM COMPONENTS FRACTIONATED BY ACRYLAMIDE GEL ELECTROPHORESIS

Biological activities of individual bands of the phosphate gel shown in FIG. 12 were tested.

The 1.5 ml remaining of the ultrafiltration sample of the previous section was chromatographed and tested. The concentration of the sample was adjusted with the same loading buffer consisting of 100 mM Tris.phosphate (pH 6.9), 0.1% SDS. The adjusted sample was then incubated at 60° C. for 30 minutes before loading.

The acrylamide gel was prepared in the same way as in the previous section, except that the thickness of the gel was 1 mm. The loading volume was 20 µl per well. The gel was pre-run for half an hour and the sample was run at constant voltage of 100 V for two hours. The total volume of 1.5 ml was run in 10 gels.

The materials of higher molecular weight were not tested. The five bands from TA to TE were cut out after staining with comassie blue. The respective bands were pooled and ground up in small pieces in a siliconized glass tube and soaked in 5 ml of buffer consisting of 10 mM Tris.Cl (pH 7.2), 50 mM NaCl, 1 mM DTT, 1 mM PMSF and 0.1% Triton X-100 for 24 hours at 4° C. The soaking buffer was then transferred to a spectrophor dialysis bag with MWCO 3,500. The materials were dialyzed against 100×volume of buffer consisting of Tris.Cl (pH 7.2), 50 mM NaCl and 1 mM DTT at 4° C. for 48 hours making 5 changes of buffer. The dialyzed samples were then concentrated to 500 µl with an Amicon 10 ml capacity concentrator using YM 3 membrane with MWCO 3,000.

The sample (80 µl) was diluted to 800 µl with water and the protein concentration estimated with Belford reagent. The concentration of the materials were adjusted with the dialysis buffer to a concentration of 12 µg per 100 µl.

Sixteen male Sprague-Dawley rats were parathyroidectomized for testing with tetracycline labelling as described above. Their pre-PTX and post-PTX serum calcium levels were 2.51 (S.D.=0.002) and 1.53 (S.D.=0.001) respectively. Test materials (200 µl) were injected in each animal. Four rats were used for testing the activity of the material eluted from each band. Four rats of a control group were injected with 200 µl of the carrier buffer.

Three bands out of the five collected contained enough material for testing. The amounts of materials available were 50 µg for Band TE, 55 µg for Band TB and 59 µg for Band TA. Protein concentrations for Bands TC and TD were too low to be detected and these bands were not tested. One rat receiving TA and one rat receiving TB died of anaesthesia during tail vein puncture.

Figure 13:
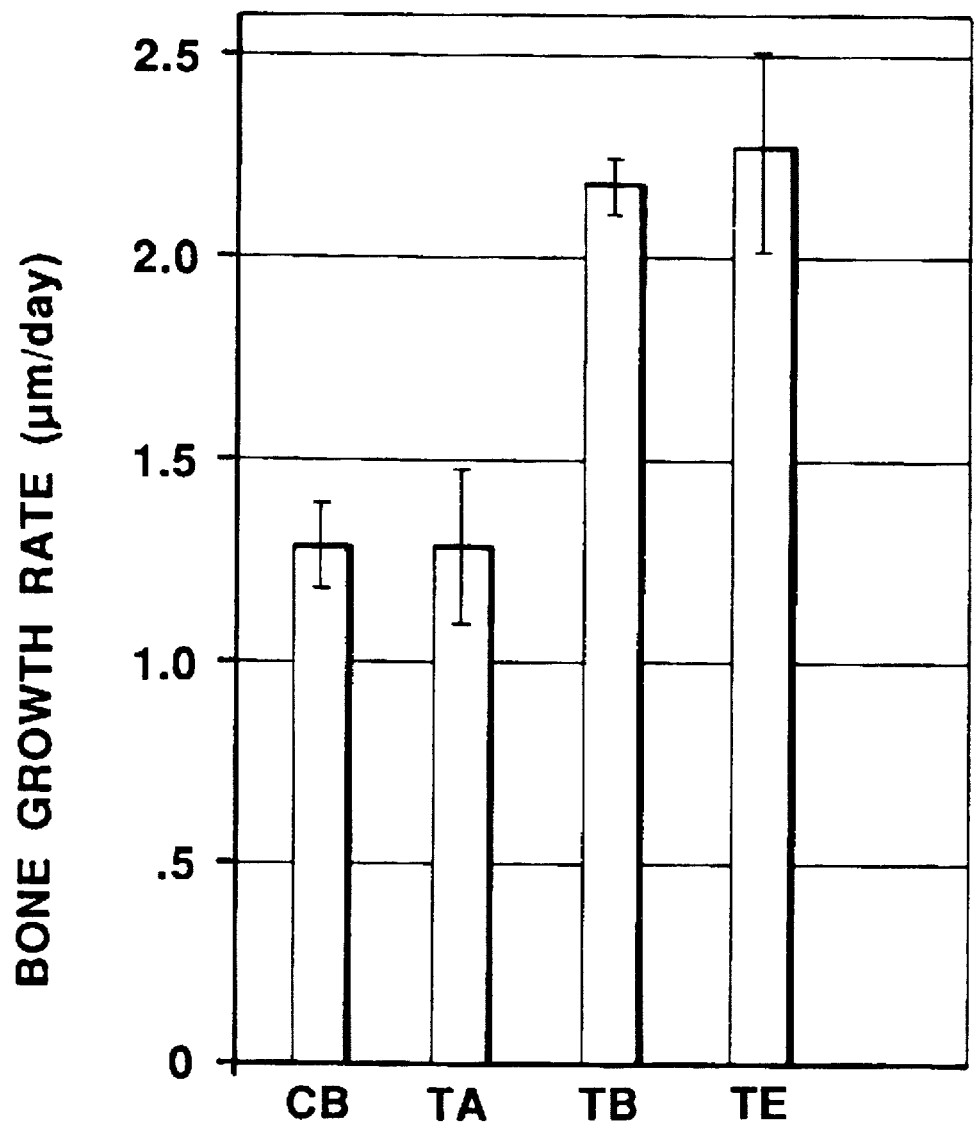
FIG. 13 shows biological activities of material eluted from bands in acrylamide gel electrophoresis. The bands in the gels were cut out, pooled accordingly and soaked in 20 mM Tris.Cl (pH 7.2), 50 mM NaCl, 0.1% Triton X 1 mM DTT and 1 mM PMST for 48 hours. The eluted materials were extensively dialyzed against a buffer of 20 mM Tris.Cl (pH 7.2); 50 mM NaCl, 1 mM PMST-and 1 mM DTT with MWCO membrane of 3.5K and concentrated to 500 ml. The protein contents were determined by Belford Reagent and 24 µg of material were tested in pre-parathyroidectomized rats as before. Four animals were used for the control group which received the carrier buffer. Only bands TA (N=3), TB (N=3) and TE (N=4) contained enough material for testing. TB and TE showed significant stimulant effect on bone formation (P<0.025) whereas TA showed no effect. The error bars indicate±1 standard deviation (S.D.).

FIG. 13 shows the effects of the test materials on the bone mineral apposition rate in the parathryoidectomized rats. Control rats receiving the buffer showed an apposition rate of 1.27 µm/day (S.D.=0.21). Rats receiving the test materials showed rates of 1.27 µm/day (S.D.=0.21), 2.14 µm/day (S.D.=0.14) and 2.24 µm/day (S.D.=0.28) for bands TA, TB and TE respectively. The rates for Band TB and Band TE were significantly higher than those of the control and Band TA (P<0.025). It appears that the control rat in this experiment was higher than the previous experiment, for reasons which are unclear.

There thus appear to be at least two active polypeptides having molecular weights of about 6 to 6.5 kilodaltons (TB) and 12 to 13 kilodaltons (TE), the relationship between the two peptides being unknown on the basis of these results.

DETERMINATION OF AMINO ACID SEQUENCES OF BANDS ISOLATED FROM ELECTROPHORETIC FRACTIONATION OF RAT SERUM COMPONENTS

MATERIALS AND METHODS

About 100 µl of material from the previous ultrafiltration was used for sequencing. The material was diluted to a concentration of 100 µg in 15 µl using buffer of the following composition: 100 mM Tris.phosphate pH 6.9; 0.1% SDS; 1 mM DTT; and 50 mM NaCl. Phosphate gel electrophoresis was carried out in the same manner as described in the previous section. The thickness of the gel was 1 mm.

The 100 µl of material was loaded in 5 lanes and BDH low molecular weight markers were used.

A small Hoeffer protein transfer unit was used. The gel was put onto a PVDF membrane (Millipore) and transferred at constant voltage of 250 V for 1 hour. A double layer of membrane was used to ensure all proteins in the gel were trapped by the membrane. After the transfer, the membrane was stained with comassie blue. Individual bands were cut off for labelling.

The sequences were determined in a sequencing laboratory according to well known procedures:

TB sequence (SEQ ID NO:1): Gly Pro Gly Gly Ala Gly Glu Thr Lys Pro Ile

TE sequence (SEQ ID NO:2): Gly Pro Gly Gly Ala Gly Glu

The TB and TE were thus found to be related peptides in that at least the first six amino acids of their N-terminal ends have the same amino acid sequences. It is not clear from these results whether TB is an active fragment of TE or TE is a dimer or polymer of TB.

the plaque reached a diameter of slightly less than 1 mm, plates were refrigerated at 4° C. overnight. On the following day, a nitrocellulose filter paper (0.45 u from Amersham) was layered on top of the soft agarose and left for 3 minutes. Using a needle the membrane was pierced at three or more asymmetric locations into the agar plate for future alignment of the membrane (or radiograph of it) to the plates. The membrane was then lifted and placed DNA side up onto a culture plate containing 0.4N NaOH and floated in the position for 20 minutes. It was then transferred to 6xSSC for 20 minutes and air dried for hybridization.

A 32 mer oligonucleotide probe was synthesized with a Cyclone-plus oligonucleotide synthesizer (Milligen) using phospoarmidite chemistry. The probe was synthesized with the DMT group left intact for subsequent purification by reverse phase HPLC. The probe was synthesized on a 0.2 µmole scale. After the synthesis, the probe was deprotected with 4 ml of ammonium hydroxide for 24 hours at room temperature. The deprotected material was dried in a Speed-vac concentrator in 4 aliquots. The nucleic acid probe used has the following sequence (SEQ ID NO:3):

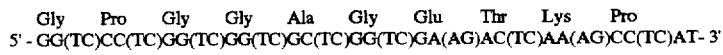

Gly Pro Gly Gly Ala Gly Glu Thr Lys Pro
5'- GG(TC)CC(TC)GG(TC)GG(TC)GC(TC)GG(TC)GA(AG)AC(TC)AA(AG)CC(TC)AT- 3'

EXPERIMENTS INVOLVING SYNTHETIC HUMAN POLYPEPTIDE
SCREENING OF HUMAN cDNA LIBRARY FOR DNA SEQUENCE ENCODING THE CIRCULATING POLYPEPTIDE

A nucleic acid probe was synthesized on the basis of the amino acid sequence determined for polypeptide isolated from rat serum and a human cDNA library screened. A major site for the synthesis of circulating serum peptides and proteins is known to be the liver and it has been reported that patients suffering from chronic liver failure often suffer bone loss. For this reason, a human cDNA library derived from liver tissue was screened.

MATERIALS AND METHODS
ISOLATION OF cDNA FROM FETAL LIBRARY

A human cDNA library from Clontech was used. The library was prepared from a human fetus with unspecified sex at 22 weeks gestation. The mother had blood type O (catalogue #HL1064A). The liver mRNA isolated was primed by oligodT primer and using reverse transcriptase, the first strand of cDNA was synthesized. This was followed by S1 nuclease digestion and synthesis of the second strand by DNA polymerase. The blunt-ended double strain cDNA was ligated to an ECoR 1 linker and cloned into lambda gt10.

The cDNA library was then propagated. A series of dilutions of the library was made with SM medium. A culture of E. coli C600 hfl in LB broth with 0.2% maltose was made and this was cultured in a steady late growth phase (usually an overnight culture). A 100 µl volume of the diluted library suspension was added to 300 µl of SM and 600 µl of the overnight E. coli C600 hfl culture and incubated for 20 minutes at 37° C. The suspension was then put in 3 ml of 0.7% agarose top agar and kept in a molten state at 50° C. This was immediately poured onto a 90 mm circular LB agar plate prewarmed at 37° C. The top soft agarose was allowed to solidify at room temperature, and the culture plates were then incubated at 37° C. until plaques were visible, that is, a little less than 1 mm in diameter. The dilution at which the titre gave to 30,000 plaques per plate was noted and used for future propagation.

The cDNA libraries were then immobilized on nitrocellulose membranes. The cDNA libraries were each plated at a concentration of 30,000 plaques per 90 mm plate. When The bases within parentheses indicate degenerate codons. The hypothetical protein to which the nucleic acid corresponds is given the identifier SEQ ID NO:4.

The probe was purified by reverse phase HPLC. An aliquot of the dried material was dissolved in 1 ml of 100 mM TEAA (pH 7.0). The sample was filtered through a Hewlett Packer sample filter and loaded onto a C18 semi-prep Beckman column, 7.5×150 mm. The sample was chromatographed the Beckman equipment as described previously. The gradient program was as follows:

| Solvent A: 100 mM TEAA pH 7.2 Solvent B: Acetonitrile | | | |
|---|---|---|---|
| Time (minutes) | | | Duration |
| 0 | 95% A | 5% B | |
| 5 | 80% A | 40% B | 15 |
| 25 | 50% A | 50% B | 10 |
| 40 | 95% A | 5% B | 5 |
| 65 | END | | |

The failure sequence eluted first and the intact sequence later at about 35 minutes. The peak was collected and dried. 1% TFA was then added to detritylate the DMT and then dried again. 3% ammonium hydroxide was added in a volume of 100 µl to neutralize the TFA remaining after drying. The material was dried again and redissolved in water. 100 µl of the dissolved material was passed through a 0.1 ml G25 spun column and then the DNA concentration was measured by absorption at 260 nm. 1 O.D. unit at 260 nm was taken to represent a concentration of about 33 µg per ml.

The probe was then kinased. 50 pmoles of the probe was kinased by T4 DNA kinase (Pharmacia) with 50 pmoles of $^{32}P$ labelled ATP with activity of >3,000 Ci per mMole and 10 uCi/µl (Amersham).

The probe was then hybridized with the DNA immobilized on the nitrocellulose membrane. The dried nitrocellulose membranes were incubated at 42° C. in prehybridization solution for two hours. The volume was 50 ml. The labelled 50 pmole probe was then added and allowed to hybridize at 42° C. overnight. The number of membranes was 50 in 50 ml of hybridization solution. The following day, the membrane was washed with 300 ml of 2×SSC four times at room temperature, about 5 minutes each time. The membranes were then incubated in 50 ml of 1×SSC at 68° C. for 1 hour, rinsed in 1×SSC at room temperature once and dried. A 1 µl volume of a radioactive ink (0.5 ml giving a cps of 1000) was spotted onto each punctured part of the filter for marking the position of the membrane. The membranes were then exposed to Amersham hyper film for 18 hours at 85° C. with an intensifying screen. The film was developed and aligned with the agarose plates for the identification of the clone. The positive clone was picked and re-propagated once in agarose plate and rehybridized for confirmation.

One positive clone was identified after screening about 300,000 plaques.

AMPLIFICATION OF cDNA SEQUENCE OF THE HUMAN CIRCULATING BONE GROWTH FACTOR

The cDNA clone was amplified according to procedures of Maniatis et al. (27). The positive plaque HL 1-7 was picked by a sterile pasteur pipette and placed in 1 ml of 60% SM and 40% glycerol, first at 37° C. for 2 hours and then at 4° C. overnight. One colony of *E. coli* C600 hfl was inoculated in 10 ml of LB broth with 0.2% maltose. The culture was grown overnight at 37° C. in a shaker incubator (Queue) at 200 rpm. The following morning, 100 µl of the HL 1-7 suspension was inoculated in 300 µl of SM and 600 µl of the *E. coli* C600 hfl overnight culture and incubated at 37° C. for 20 minutes. A loop of this culture was then streaked onto a LB agar plate and incubated at 30° C. until visible colonies appeared. Several colonies were selected and numbered and each colony was streaked onto two LB agar plates. One plate was incubated at 30° C. and the other at 40° C. Those colonies which grew at 30° C. only and lysed at 40° C. were used for propagation of HL 1-7.

One HL 1-7 lysogenic colony was inoculated in a 10 ml LB broth with 0.2% maltose, and cultured in a shaker incubator at 30°C. until the culture became dense. The O.D. was measured at 600 nm. 1 O.D. unit at 600 nm was taken to represent a concentration of *E. coli* of $8 \times 10^8$ cells per ml. A 500 ml volume of prewarmed NZCYM medium was used to inoculate $10^{10}$ cells and another 500 ml of medium was similarly inoculated. Both bottles of medium were cultured overnight in a shaker incubator at 200 rpm and at 37° C. The following morning, 10 ml of chloroform were added to each of the 500 ml cultures and incubation continued for 30 minutes. DNAse and RNAse A were added to a concentration of 1 µg per ml after the cultures were cooled to room temperature. The cultures were kept at room temperature for half an hour and NaCl added to a concentration of 1M. The cultures were left on ice for one hour and then the bacterial debris was centrifuged down for 10 minutes using a g force no greater than 11,000. An amount of 50 g of PEG 8000 was then added to each 500 ml of culture which were kept on ice for another hour after the PEG was dissolved. The phage was pelleted down by centrifugation at 4° C. at 11,000 g for 10 minutes and the supernatant discarded. The precipitate was resuspended with 16 ml of TM and the solution extracted once with an equal volume of chloroform. To the aqueous phase was added 4 ml of glycerol and gradient centrifugation was carried out as follows.

A layer of CsCl (s.gr 1.6) was added to the bottom of an ultraclear Beckman ultracentrifuge tube, and a layer of CsCl (s.gr. 1.4) was layered on top of the bottom layer. The HL 1-7 suspension was layered onto the CsCl gradient and centrifuged at 35,000 rpm at 4° C. for 2 hours in a Beckman L8-70 ultracentrifuge using a T:60 fixed angle rotor. The phage particles appeared as a blue band between the two layers of CsCl gradient. Using a needle attached to a syringe, the phage particles were sucked out from the centrifuge tube by puncturing through the wall. The suspension was extracted once with phenol, then once by phenol/chloroform 1:1 and then twice by chloroform. The phage DNA was recovered by ethanol precipitation (the addition of NaCl to a concentration of 0.5M and 2 volumes of ethanol and freezing at –85° C. for 10 minutes). The amount of DNA present was estimated by absorption at 260 nm.

The DNA insert was then sized by agarose gel electrophoresis. A 15 µg amount of HL 1-7 DNA was digested in a 150 µl volume of digestion buffer consisting of 2×Pharmacia one-phor-all buffer. Digestion was carried out with 25 units of ECoR1. (Pharmacia) at 37° C. for 1.5 hours. After digestion, the DNA was purified by phenol chloroform extraction and ethanol precipitation as described above. A 0.5 cm thick 1.2% SEAKEM# GTG grade agarose gel was poured. A comb with five 8 mm wide wells was used. The digested DNA was loaded into one well and Pharmacia Φ×174 marker used as standard. The gel was run in TBE buffer at 8 V per cm of gel. The gel was then stained with ethidium bromide.

A 10 µg/ml concentration of DNA solution in water was used for sizing by capillary electrophoresis. The running buffer was 89 mM boric acid and 89 mM Tris pH 8.5, 2 mM EDTA and 0.5% hydroxypropylmethyl cellulose (Sigma). The instrument was a Beckrman capillary electrophoresis unit, Model 2100. The sample was introduced into a 27 cm long DB17 coated capillary tube with 100 µm internal diameter (J&W Scientific Inc) by electrokinetic force at 7 kV for 7 seconds. This was followed by pressure injection of a water plug by pressure injection for 5 seconds. Electrophoresis was carried out at constant voltage of 6.25 kV for 12 minutes. The absorption at 260 nm was recorded with Beckman System Gold Software. Boehringer Manhein DNA molecular marker VI was used as a standard.

Phage DNA was then subjected to PCR amplification. The phage DNA was precipitated from 1 ml of phage suspension by ethanol precipitation. Proteins associated with the phage were stripped with 4M sodium perchlorate and two extractions with phenol/chloroform followed and then two more extractions with chloroform were carried out. The DNA was recovered by ethanol precipitation twice and washing with water through centricon 30 (Amicon). The final volume of the DNA solution was adjusted with water to 0.5 ml.

PCR was carried out with a thermocycler (M.J. Research Inc.). The buffer consisted of 50 mM KCl, 10 mM Tris.Cl (pH 8.3), 2.5 mM $MgCl_2$, 0.1% gelatin, 0.45% Tween 20 and 0.45% NP 40. The buffer contained 50 pmoles of each of the amplification primers (Clontech cat. #5411), 0.125 mM of dNTPs, 1M DTT and 2.5 units of Taq DNA polymerase. A 10 µl volume of the purified phage was used as template. One primer primes with the DNA at the Hind III site 5' upstream the ECoR1 site and has the following sequence: 5'-AAG CTT CAC ACC ACG AAC CAG -3' (SEQ ID NO:5). The other primer primes the sequence of HL 1-7 3' down stream of the ECoR1 site and had the following sequence: 5'-TTA TGA GTA TTT CTT CAA GGG -3' (SEQ ID NO:6).

The PCR program was as follows:

| Step (minutes) | Temperature (°C.) | Time |
|---|---|---|
| 1 | 95 | 5 |
| 2 | 56 | 1 |
| 3 | 74 | 3 |
| 4 | 95 | 1 |
| 5 | 56 | 1 |
| 6 | 74 | 3 |
| 7 | cycle to steps 4–6 × 30 cycles | |
| 8 | 95 | 1 |
| 9 | 56 | 1 |
| 10 | 74 | 7 |
| 11 | 4 | 5 |
| 12 | stop | |

The product was extracted with chloroform/phenol once, chloroform twice, ethanol precipitated and redissolved in 100 µl of water. The yield of the phage DNA was about 15 to 18 µg per litre of culture. The recovered DNA was reasonably pure with a 260 to 280 ratio of approximately 1.7.

The result of the sizing by both agarose electrophoresis and capillary electrophoresis shows the size of the insert to be about 300 base pairs. The size observed in capillary electrophoresis is about 600 base pairs, but this includes an extra 285 base pair 5' from the vector (from the Hind III to the ECoR1 site.)

SEQUENCING OF PHAGE HL1-7 cDNA

EXPRESSION OF DNA SEQUENCE ENCODING PART OF THE cDNA SEQUENCE DERIVED FROM HUMAN FETAL LIVER cDNA LIBRARY

The following sequence was synthesized by oligonucleotide synthesis for cloning into a plasmid, for expression.

```
         ECoR 1                    START  Gly  Ile  Gly  Lys  Arg  Thr  Asn  Glu  His  Thr
      5'- AATTCTTAGGATCCTAGGATG           GGG  ATC  GGA  AAA  CGA  ACA  AAT  GAA  CAT  ACG
             GAATCCTAGGATCCTAC            CCC  TAG  CCT  TTT  GCT  TGT  TTA  CTT  GTA  TGC

Ala  Asp  Cys  Lys  Ile  Lys  Pro  Asn  Thr  Leu  His  Lys  Lys  Ala  Ala  Glu
         GCA  GAT  TGT  AAA  ATT  AAA  CCG  AAC  ACC  TTG  CAT  AAA  AAA  GCT  GCA  GAG
         CGT  CTA  ACA  TTT  TAA  TTT  GGC  TTG  TGG  AAC  GTA  TTT  TTT  CGA  CGT  CTC

Thr  Leu  Met  Val  Leu  Asp  Gln  Asn  Gln  Pro  TER
         ACT  TTA  ATG  GTC  CTT  GAC  CAA  AAT  GAA  CCA  TAA  AGA  TCT  TGA  TCGA       -5'
         TGA  AAT  TAC  CAG  GAA  CTG  GTT  TTA  CTT  GGT  ATT  TCT  AGA  ACT  HIND I I I
```

A 15 µg amount of the phage DNA was denatured with sodium hydroxide and precipitated with sodium acetate (pH 4.5) and ethanol. It was annealed with one of the primers (Clontech Cat# 6184 and 6186). Sequencing was carried out by Sanger dideoxy chain termination using a Pharmacia T7 DNA polymerase sequencing kit. $^{32}$P dATP (Amersham sp. activity>3,000 Ci/mMole and 10 µCi/µl was used as radiolabel). Sequencing was carried out in a 45 cm long gel using the Base Runner Unit (IBI). Sequencing was carried out at constant power of 45 watts. The gel was dried after the run and exposed to Amersham Hyperfilm overnight at –85° C. and developed.

The results of the sequencing are shown below. The mature cDNA encodes 53 amino acids. The first 17 of which may represent a signal sequence.

The sense strand of the above-listed nucleic acid sequence is identified as SEQ ID NO:9; the anti-sense strand of the sequence is identified as SEQ ID NO:10; and the above-listed polypeptide sequence is identified as SEQ ID NO:11.

In this construction there are two restriction sites for ligation into a pUC 8 plasmid spliced by ECoR 1 and Hind III. The constructed plasmid was then introduced into the JM 103 strain of *E. coli*. The transformed clones were selected by plating the bacteria onto a LB agar plate containing 35 µg per ml of ampicillin.

The sequence constructed excludes what is thought to be a signal sequence coded for in the cDNA clone. The amino acid sequence Gly-Ile-Gly-Lys-(peptides 1–4 of SEQ ID

```
5'- TTT  GGC  TTT  ATT  CAT  AGC  GGT  AAT  TAA  TGA  TCA  AGA  CAG  TTG  ATT  ACT

Met  Thr  Ala  Gln  Asn  Thr  Asp  Leu
    CGT  AAG  CAC  TAT  TAA  AAA  TTT  GCA       ATG  ACT  GCT  CAA  AAT  ACA  GAC  CTT

Asn  Glu  Leu  Ser  Asn  Ser  Phe  Thr  Leu  Gly  Ile  Gly  Lys  Arg  Thr  Asn
    AAC  CAA  CTA  TCC  AAC  AGT  TTC  ACT  TTA  GGG  ATC  GGA  AAA  CGA  ACA  AAT

Glu  His  Thr  Ala  Asp  Cys  Lys  Ile  Lys  Pro  Asn  Thr  Leu  His  Lys  Lys
    GAA  CAT  ACG  GCA  GAT  TGT  AAA  ATT  AAA  CCG  AAC  ACC  TTG  CAT  AAA  AAA

Ala  Ala  Glu  Thr  Leu  Met  Val  Leu  Asp  Gln  Asn  Gln  Pro  TER
    GCT  GCA  GAG  ACT  TTA  ATG  GTC  CTT  GAC  CAA  AAT  CAA  CCA  TAA  AGG  ATC

TGC  AGC  TTA  TGT  CTT  CTA  GTT  TAT  CTT  TTG  CAT  AAA  AAA  GCT  GCA  GAG

ACT  TTA  ATG  GTA  ATT  GCC  AAA  ATC  AAC  CAT  AAA  GGA  TCT  GC                -3'
```

The above-listed nucleic acid sequence is identified as SEQ ID NO:7; the amino acid sequence is identified as SEQ ID NO:8. The size of the polypeptide minus the leader is about 4000. This is comparable to the size of band TB of the polypeptide isolated from rat serum.

A nucleic acid sequence containing a portion of the above sequence, identified as SEQ ID NO:9, was next cloned into a plasmid for expression, as described in the following section. It will be appreciated that a person skilled in the art would be capable of obtaining similar results using suitable vectors and expression vehicles other than those chosen here.

NO:11) bears some resemblance to the first four amino acid sequence of the rat polypeptide, it is assumed that this is the beginning of the mature peptide in the human polypeptide.

The bacteria was cultured in Terrific medium for eight hours to reach the slow growth phase. The Terrific medium consists of 17 mM potassium phosphate buffer at pH 7.2, 4% glycerol and 35 µg/ml of ampicillin in addition to the tryptone and yeast extract in the LB medium. After an eight hour culture, the bacteria were spun down for changing the medium for expression. The expression medium consisted of: 2% casamino acid; 17 mM phosphate buffer (pH 7.2); 4% glycerol; 40 µm of thiamine; 2 mM IPTG; and 35 µg/ml of ampicillin.

The bacterial pellet was resuspended in this medium in a volume equal to the original Terrific medium volume. Culturing was continued in a shaker incubator at 37° C. overnight at 200 rpm.

The culture was spun down two times (15 minutes each at 12,000 g) to pellet down the bacteria completely. The medium was then concentrated 10 times with YM3 membrane. A 1 ml volume of this material was subjected to C3 reverse phase HPLC under the same conditions as described before.

Figure 14:
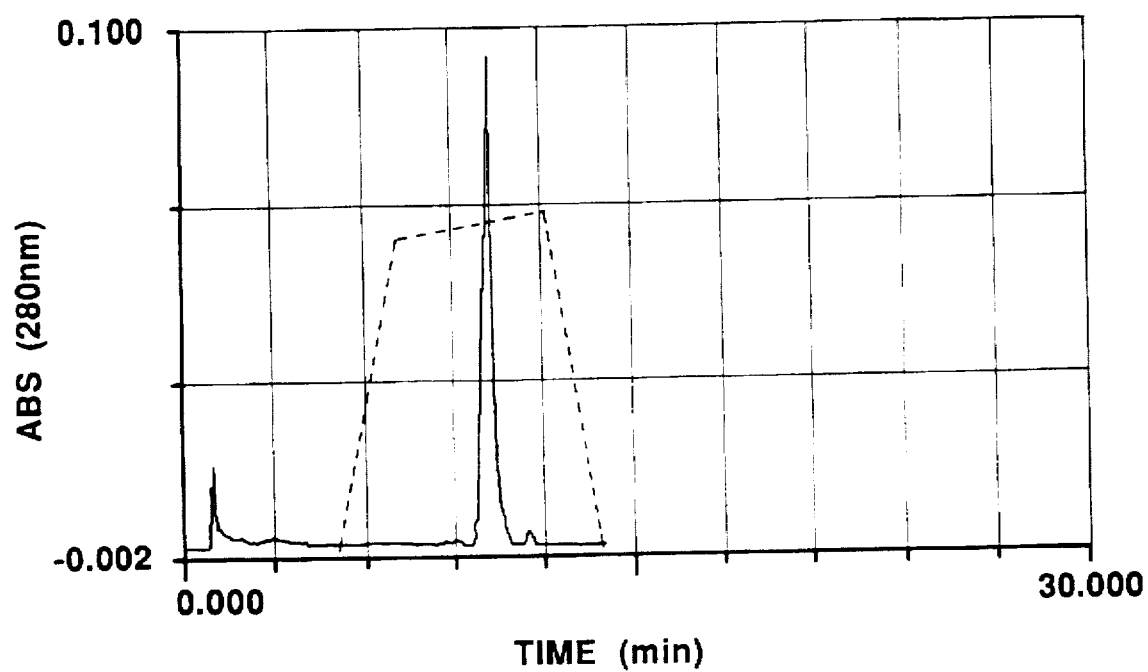
FIG. 14 is a chromatogram (HPLC on C3 column) of human polypeptide expressed in *E. coli*. The *E. coli* medium was centrifuged at 12,000 G, two times, fifteen minutes each time. It was concentrated 10 times with YMS membrane (MWCO 3K). The salt concentration of the medium was adjusted to 100 mM prior to concentration with sodium phosphate (pH 7.2). A well-resolved peak was eluted at 62–63% $CH_3CN$.

A single well resolved peak eluted at about 62–63% acetonitrile. A portion of the elution profile is shown in FIG. 14. From 50 ml of culture, about 1 mg of polypeptide was obtained through purification as estimated by Belford reagent.

BIOLOGICAL ACTIVITY OF THE EXPRESSED PRODUCT

Figure 15:
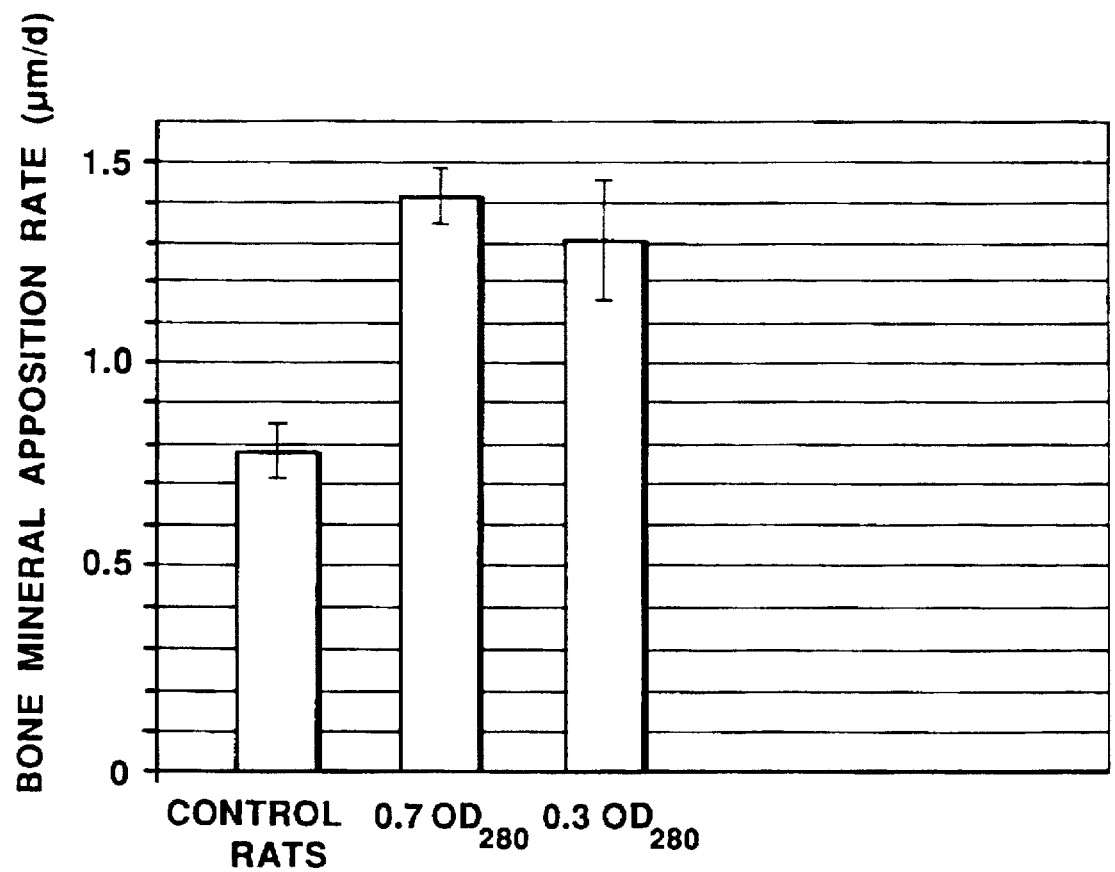
FIG. 15 illustrates the effect of human polypeptide expressed in *E. coli* on bone formation in rats. Control rats (N=6) were injected with carrier buffer. A first group of test rats (N=4) were injected with 0.7 O.D. (280 nm) units of the expressed polypeptide and a second group of test rats (N=6) were injected with 0.3 O.D. units of polypeptide. The expressed product showed biological activity (P<0.05) compared to that of the control group. The error bars indicate±1 S.D.

Intact 400–420 g male rats were used for testing. A control group received the carrier buffer of 50 mM sodium phosphate (pH 7.2). One test group received 0.7 O.D. unit of the expressed polypeptide, and another test group received 0.3 O.D. unit of the polypeptide. As shown in FIG. 15, the expressed product appears to have a stimulant effect on bone formation.

EXPERIMENTS INVOLVING CHEMICALLY SYNTHESIZED HUMAN POLYPEPTIDE

A polypeptide having an amino acid sequence corresponding to a selected nucleic acid sequence determined from the cDNA library (SEQ ID NO:7) was synthesized according to conventional solid-phase chemical methods (28). The selected sequence was as follows (SEQ ID NO:11):

Heat inactivated peptide for control group B (see next section) was prepared by dissolving 350 μl of the peptide, prepared as described earlier in this section) in deionized water. This was boiled in a capped polypropylene tube (Sarsted) in a microwave oven for 10 minutes. The solution was cooled. The vehicle prepared for the active peptide was added to this to a final volume of 14 ml. The concentration of the inactivated peptide was thus also 25 μg per ml.

Tetracycline labelling solution was prepared by dissolving 360 mg of tetracycline base (Sigma) in 50 ml of deionized water to yield a concentration of 7.2 mg per ml. Each rat weighed about 300 g so that the amount of tetracycline administered (1 ml of labelling solution) was about 24 mg per Kg body weight.

BIOLOGICAL ACTIVITY OF THE CHEMICALLY SYNTHESIZED PEPTIDE

Male Sprague-Dawley rats from Charles River Laboratory having a weight of about 250 g were used. The animals were housed singly in cages and maintained on an unlimnited diet of tap water and Purina Rat Chow.

One ml of each solution was administered intramuscularly into the thigh. There were twelve rats per experimental group:

Control Group A—Each animal received 1 ml of 0.1% BSA in 0.1% acetic acid by intramuscular injection to the right gluteus maximus. This was followed by injection of 1 ml of tetracycline labelling solution intraperitoneally.

Control Group B—Each animal received 1 ml of the 0.1% BSA in 0.1% acetic acid containing peptide which had been heated by boiling for 10 minutes (see above) by intramuscular injection to the right gluteus maximus. This was followed by injection of 1 ml of tetracycline labelling solution intraperitoneally.

| Gly | Ile | Gly | Lys | Arg | Thr | Asn | Glu | His | Thr | Ala | Asp | Cys | Lys | Ile | Lys |
|---|---|---|---|---|---|---|---|---|---|---|---|---|---|---|---|
| Pro | Asn | Thr | Leu | His | Lys | Lys | Ala | Ala | Glu | Thr | Leu | Met | Val | Leu | Asp |
| Gln | Asn | Gln | Pro | | | | | | | | | | | | |

The synthetic peptide was 99% pure based on its HPLC profile. The peptide was 30 identified independently by mass spectrometry and amino acid analysis. The observed molecular mass was determined to be 4043.36 daltons, the theoretical mass of the monomer being 4043.66 daltons. The amino acid analysis of the peptide was as follows: Asp (5) 5.23, Thr (4) 3.74, Glu (4) 4.49, Gly (2) 1.72, Ala (3) 3.09, Val (1) 1.09, Met (1) 1.04, Ile (2) 1.54, Leu (3) 3.20, His (2) 2.07, Lys (5) 4.90, Arg (1) 0.99, Pro (2) 2.15.

Prior to use, 15 mg of the polypeptide were dissolved in 15 ml of 0.1% acetic acid, divided into fifteen 1 ml aliquots, and lyophilized. The peptide was stored at −20° C.

Figure 16:
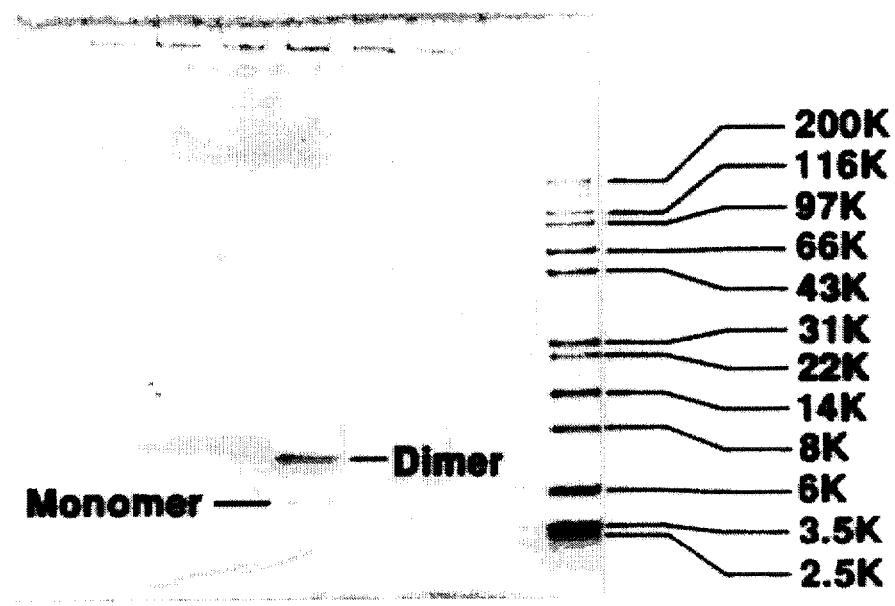
FIG. 16 shows a tricine SDS electrophoretic gel of human chemically synthesized polypeptide (SEQ ID NO:11).

Prior to testing, the synthetic polypeptide was subject to Tricine SDS gel electrophoresis. As can be seen in FIG. 16, much of the polypeptide is in the dimeric form.

The peptide test solution was prepared for administration by dissolving 1 aliquot of peptide (1 mg) in 1 ml of deionized water to give a concentration of 1 μg per μl. To 350 μl of this were added 1% heat inactivated BSA in 0.1% acetic acid (see next paragraph) to a final volume of 14 ml. A final peptide concentration of 25 μg per ml was thus obtained.

The bovine serum had been prepared by dissolving 0.5 g of BSA (Sigma) in 40 ml of deionized water. After the addition of 50 μl of acetic acid, the volume was made up to total volume of 50 ml with deionized water. The final composition was thus 1% BSA in 0.1% acetic acid. This vehicle for injection was incubated in a 56° C. water bath for 90 minutes to inactivate the BSA. The solution was stored at 4° C.

Test Group—Each animal was received 1 ml of the test solution (25 μg of peptide in 1 ml of vehicle, see above) by intramuscular injection to the right gluteus maximus. This was followed by injection of 1 ml of tetracycline labelling solution intraperitoneally.

Tetracycline labelling solution was administered to each rat again about 48 hours later. Animals were sacrificed by carbon dioxide narcosis 24 hours after the second dose of tetracycline.

Blood samples were taken by cardiac puncture immediately after expiration of the animal. About 3 ml of heparinized blood was taken for measurement of bone alkaline phosphatase. This is a serum index for bone formation. The measurements were made according to a routine conventional technique for human bone alkaline phosphatase. The results were not conclusive.

Bone samples for histological examination and for the determination of bone growth rate were chosen as follows—right femur, right tibia, right humerus, right iliac bone and the fifth lumbar vertebral body. The samples were stored at 4° C. prior to dissection.

DISSECTION OF THE RIGHT FEMUR FOR HISTOLOGICAL EXAMINATION AND FOR DETERMINATION OF BONE MINERAL APPOSITION RATE OF CHEMICALLY SYNTHESIZED HUMAN POLYPEPTIDE

Figure 17:
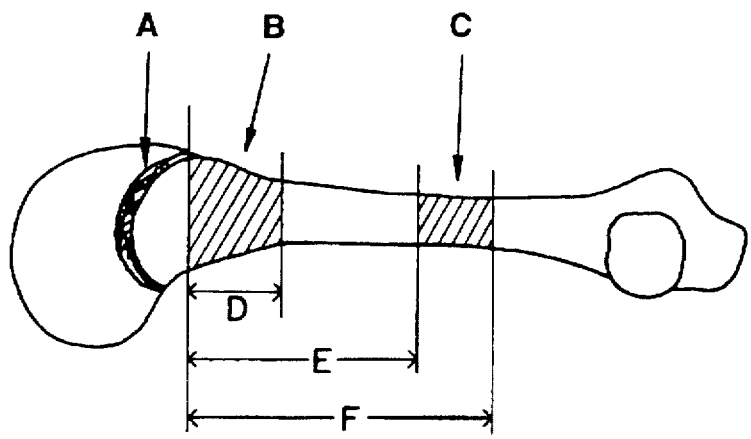
FIG. 17 shows a longitudinal sectional view of the lower right femur of a rat. The lower epiphysis is indicated by the arrow labelled A. The shaded areas represent the lower metaphysis B and midshaft C sections of the bone taken.

The muscles, tendons and periosteum attached to the right femurs of the animals of the three groups were dissected away. Cross-sections of the lower metaphysis and the midshaft of this bone were taken as described below and as illustrated in the FIG. 17.

The bone cross-sections were transferred to 80% ethanol and gently agitated overnight.

The femoral cross sections were subject to the following processing steps.

1. Dehydration through 2 changes of 100% ethanol—2 hours for each change.
2. Defatting with 100% acetone for 2 hours.
3. Acetone/Spurr's medium 1:1 overnight.

The composition of Spurr's medium is as follows:

| | |
|---|---|
| NSA (nonenyl succinic anhydride) | 130 g |
| ERL (vinyl cyclohexene dioxide) | 50 g |
| DER (diglycidyl ether of propylene glycol) | 30 g |
| DMAE (dimethylaminoethanol) | 2 g |

Bone cross sections were transferred to 100% Spurr's medium and allowed 6 hours for infiltration of the medium into the bone tissue. The medium was then replaced with a new batch of medium. 25 psi negative pressure was then applied for 15 minutes.

The cross-sections from the lower metaphysis were oriented with the lower cut surface facing the bottom of the embedding mold and polymerization of the resin, i.e., Spurr's medium, was allowed to proceed overnight at 55° C. The partially polymerized tissue blocks of the lower femoral metaphysis was then cured at 80° C. for another twelve hours. Meanwhile, the midshafts were left to sit in the liquid resin for a second night and then were cured for twelve hours at 80° C.

On the following day, one 400 µm thick section was cut at a plane midway between the two cut surfaces of the tissue blocks taken from the lower femoral metaphyses. These thick sections were ground down to a thickness by hand between two glass plates preroughened by carborundum powder (coarse with grit no. of 100) to a final thickness of approximately 8 µm. Water was used as the lubricant for grinding. The ground thin sections were then mounted unstained for examination. A section from each midshaft of the femur was similarly prepared from a plane midway between the two cut surfaces of the femoral block. The tissue sections from the femoral metaphyses were randomly coded for blind measurement of the bone apposition.

The unstained plastic embedded sections were viewed under a fluorescence microscope with a ×16 objective and ×10 eyepieces systematically to cover the trabecular bone in the space enclosed by the endosteal surface. Bone formation sites with the two tetracycline bands sharply defined were randomly chosen for measurements, the procedure being taken to minimize the error due to oblique cuts through the formation surfaces. The distance between the two tetracycline bands in um was recorded and divided by 2 (the labelling interval being two days) to obtain the rate in µm per day. Thirty randomly chosen sites from each animal were measured and the arithmetic mean used for statistical analysis.

Figure 18:
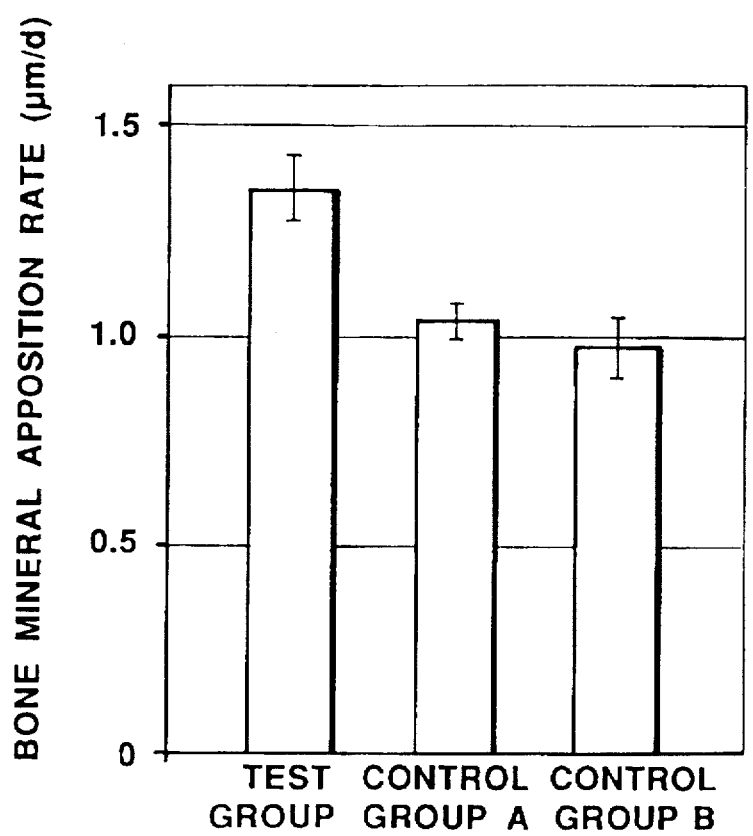
FIG. 18 shows the bone apposition rate (µm per day) in intact rats injected with 25 µg of the chemically synthesized human polypeptide, the first bar (N=9). Control Group A, the second bar, (N=9) was injected with a 1 ml solution of 0.1% BSA in 0.1% acetic acid. Control Group B, the third bar, (N=7) was injected with a 1 ml solution of 0.1% BSA in 0.1% acetic acid which had been boiled for ten minutes to denature the BSA.

The results are tabulated in Table Two and shown in FIG. 18.

TABLE TWO

| Comparison of the Group Arithmetic Means Among Groups | | | |
|---|---|---|---|
| | Test Group | Control Group A | Control Group B |
| Mean | 1.35 µm/d | 1.03 µ/d | 0.99 µm/d |
| S. D. | 0.08 µm/d | 0.04 µm/d | 0.07 µm/d |
| N | 9 | 9 | 7 |

| | t | d.f | p |
|---|---|---|---|
| Test Group vs Control Group A | 11.18 | 16 | <0.001 |
| Test Group vs Control Group B | 3.96 | 14 | <0.005 |
| Control Group A vs Control Group B | 0.62 | 14 | >0.5 |

DOSE DEPENDENT EFFECT OF CHEMICALLY SYNTHESIZED PEPTIDE ON BONE GROWTH

Forty male Sprague-Dawley rats divided into four groups of ten. The mean weight of groups 1 through 4 were 294, 297, 296 and 279 gm, respectively.

As in the previous set of experiments, a stock solution of peptide having a concentration of 1 mg per ml was prepared in 1% acetic acid. BSA was omitted. Three solutions each having a different concentration of the chemically synthesized polypeptide were prepared as follows:

Peptide solution 1: 1.1 ml of the stock solution was diluted to 5.5 ml with 0.1% acetic acid to give a peptide concentration of 100 µg per 0.5 ml of solution.

Peptide solution 2: 0.55 ml of the stock solution was diluted to 5.5 ml with 0.1% acetic acid to give a peptide concentration of 50 µg per 0.5 ml volume.

Peptide solution 3: 0.3 ml of the stock solution was diluted to 6 ml with 0.1% acetic acid to give a peptide concentration of 25 µg per 0.5 ml volume.

Tetracycline labelling solution was prepared by dissolving 288 mg of tetracycline base in 40 ml of deionized water to yield a concentration of 7.2 mg per ml. Each rat was administered (see below) with 1 ml of solution, that is about 2A g per kg b.w.

The four groups of rats were treated as follows:

Test Group A—Each animal received 1 intramuscular injection of 0.5 ml peptide solution 1 (100 µg of peptide), followed by 1 ml of tetracycline solution intraperitoneally.

Test Group B—Each animal received 1 intramuscular injection of 0.5 ml of peptide solution 2 (50 µg of peptide), followed by 1 ml of tetracycline solution intraperitoneally.

Test Group C—Each animal received 1 intramuscular injection of 0.5 ml of peptide solution 3 (25 µg of peptide), followed by 1 ml of tetracycline solution intraperitoneally.

Control Group D—Each animal received 1 intramuscular injection of 0.5 ml of 0.1% acetic acid, followed by 1 ml of tetracycline solution intraperitoneally. Each rat receives no peptide.

The second tetracycline labelling solution was prepared by dissolving 288 mg of tetracycline base (Sigma) in 40 ml of deionized water to yield a concentration of 7.2 mg of tetracycline per ml.

Each rat received 1 ml of tetracycline labelling solution (about 24 mg per Kg body weight) intraperitoneally about forty-eight hours after the initial administration and sacrificed by carbon dioxide narcosis about twenty-four hours later.

Approximately 3 ml of post mortem blood was taken from each rat by cardiac puncture and put into a heparinized tube. The plasma was then store frozen at −20° C.

The following bone samples were dissected out from each animal:both femoral bones, both tibial bones, both iliac, bones and first two tail vertebrae. These bone samples were fixed in 10% formaldehyde buffered to pH 7.4 with 20 mM of phosphate buffer.

DISSECTION OF THE RIGHT FEMUR FOR DETERMINATION OF DOSE DEPENDENCY OF BONE MINERAL APPOSITION RATE

Figure 19:
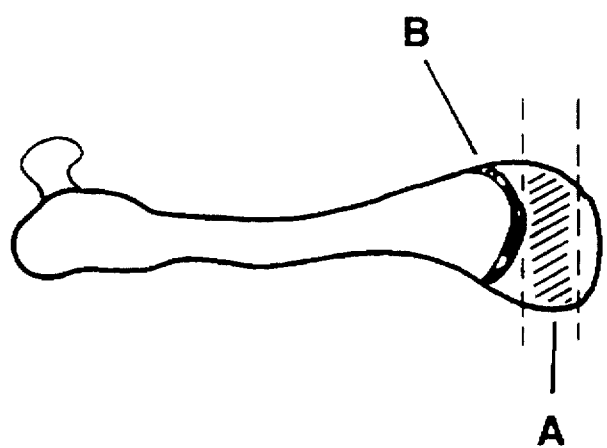
FIG. 19 shows a longitudinal sectional view of the lower right femur of a rat.

The lower epiphysis of the right femur was studied instead of the lower metaphysis. The lower femoral epiphysis was dissected out as illustrated in FIG. 19.

The bone tissue was gently agitated for 6 hours in 80% ethanol and then transferred to 95% ethanol. The following day the bone tissue was transferred to 100% ethanol, which was changed after eight hours. The following day, the bone tissue was transferred to acetone. After about twenty-seven hours, the tissue was transferred to a 1:1 mixture of acetone and Spurr's medium. After about eighteen hours the tissue was transferred to 100% Spurr's medium and gently agitated for about twenty-four hours. The Spurr's medium was changed and the tissue was incubated at 37° C. for another twenty-four hours. At this point, the blocks from the lower epiphysis appeared to be partially polymerized, that is the plastic had turned into a thick jelly. The blocks were transferred to an incubator and cured at 45° C. for about 4 ½ hours to harden the embedding medium. A fmal curing step at 80° C. was carried out for four hours.

A 400 μm section was cut at a level of the bone block 1 mm below the upper cut surface. This thick section was ground down to a final thickness of about 8 μm by hand between two ground glass plates which had been pre-roughened with coarse carborundum powder. Water was used as the lubricant during the grinding. These thin sections were mounted unstained in Permount (Fisher).

The method of measurement described in connection with the previous set of experiments was used. The rate was measured at 30 bone formation sites in the trabecular bone enclosed by the endosteal surface of the lower femoral epiphysis. The whole sectional area was covered systematically in the manner shown in FIG. 20. Samples were coded prior to measurement.

The results are summarized in Table Three.

TABLE THREE

| Comparison of the Arithmetic Means Among Groups | | | |
|---|---|---|---|
| | Group A (100 μg) | Group B (50 μg) | Group C (25 μg) | Group D (0 μg) |
| Mean (μm/day) | 1.32 | 1.15 | 1.05 | 0.85 |
| S. D. | 0.07 | 0.05 | 0.03 | 0.04 |
| GROUP | t | d. f. | p |
| A vs B | 6.64 | 8 | <0.01 |
| B vs C | 5.46 | 8 | <0.01 |
| C vs D | 13.80 | 8 | <0.01 |

The results of Table Three are graphically illustrated in FIGS. 21 and 22. These results indicate that the stimulant effect in rats of the chemically synthesized polypeptide increases with the amount of peptide administered within the dosage range and time interval used.

TOXICITY EXPERIMENTS INVOLVING N-TERMINAL ACETYL CHEMICALLY SYNTHESIZED POLYPEPTIDE

A miniosmotic pump (Alzet) was loaded with about 1.5 ml of the chemically synthesized peptide having an N-terminal acetyl group (SEQ ID NO:12) in 0.1% acetic acid so as to give a calculated daily delivery of about 25 μg per day. A pump was implanted under the subcutaneous fascia of the dorsal aspect of the left side of the thorax of five rats which had been parathyroidectomized seven days earlier. Five similarly parathyroidectomized rats received similar implants containing only 0.1% acetic acid. Five intact rats were also used as controls.

Twenty-eight days later 0.5 ml of an aqueous solution of tetracycline hydrochloride was injected intramuscularly into the right gluteus maximus of each of the implanted rats, as described previously. Another 48 hours later, a second injection of tetracycline hydrochloride solution was injected. The rats were sacrificed another 24 hours later.

The bone mineral apposition rate was determined by examination of a cross-section of the lower metaphysis of the right femur of each of the ten rats which had been given implants. The results are summarized in Table Four and depicted graphically in FIG. 23.

TABLE FOUR

| Comparison of the Group Arithmetic Means Among Groups | | |
|---|---|---|
| | Test Group | Control Group |
| Mean | 1.27 μm/d | 0.67 μm/d |
| S. D. | 0.18 μm/d | 0.08 μm/d |
| N | 5 | 5 |
| | t | d. f |
| Test Group vs Control Group | 7.14 | 8 |

Histological evaluation of selected tissues of the five rats of each of the groups indicated in Table Four were carried out microscopically. No evidence of toxic lesions was found.

EXPERIMENTS INVOLVING OVARIECTOMIZED RATS AND THE NORMAL CHEMICALLY SYNTHESIZED POLYPEPTIDE. ADMINISTRATION OVER A FOUR WEEK PERIOD

Ovariectomies were performed on six female Sprague-Dawley rats, each sedated with 1 mg of sodium barbiturate I.P. Sham operations were carried out a second group of six rats. The rats were given two weeks to recover from the operations.

The six ovariectomized rats were injected subcutaneously with 100 μl of a 0.1% acetic acid solution containing 100 μg of the chemically synthesized peptide (SEQ ID NO:11) every 24 hours for 28 days. On day 25, a tetracycline hydrochloride solution was injected intramuscularly into each rat so as to give 24 mg per Kg of body weight, as described previously. On day 27, a second dose of tetracycline hydrochloride was injected and the rats were sacrificed on the 28th day.

A second group of six ovariectomized rats, was similarly treated with a 0.1% acetic acid solution containing no peptide over the same 28 day period. A third group of six rats, each of which had undergone the sham operation, was similarly treated with a 0.1% acetic acid solution containing no peptide over the same 28 day period. A fourth group of six intact rats was similarly treated with a 0.1% acetic acid solution containing no peptide over the same 28 day period.

Postmortem blood was taken by cardiac puncture and serum frozen until analyzed. A full autopsy was performed on each rat. No ill effects were observed in the rats treated with the polypeptide.

Each of the right femurs was dissected out from its soft tissue, fixed for two days, and X-rays taken at 70 kV for 1 min., 2 min., and 3 main. The 3 minute exposures gave the most satisfactory results. The bone densities of the femurs from the second group of rats, the ovariectomized rats not treated with the peptide, showed a visibly lower bone density.

The right femur of each rat was decalcified separately. The decalcification fluid consisted of 10% formic acid (v/v) and 5% sodium citrate (w/v) at pH 3.0. Each bone was placed in 6 ml of the decalcification fluid. The fluid was replaced after 4 days, again after another 4 days, again after another 2 days, and again after another 3 days. After another 2 days, the decalcification fluid was removed and replaced by deionized water, and the sample agitated for 2 days. The water changed after two days and again after another day. After another day, all of the fluid samples for each rat were combined and the final volume of each adjusted to 50 ml with deionized water.

The volume of each right femur was determined by determining the volume of water displaced when the bone was immersed in water. The calcium concentration of each sample was determined according to standard methods and the calcium density of each bone calculated. The results are tabulated in Table Five and graphically depicted in FIG. 24. As can be seen, the bone calcium concentration measured for the ovariectomized rats treated with the peptide (SEQ ID NO:11) appears to be normal, while the calcium concentration of the untreated ovariectomized rats is depressed.

TABLE FIVE

Right Femoral Calcium Concentration of Ovariectomized Rats

| | Group A | Group B | Group C | Group D |
|---|---|---|---|---|
| Mean (μmol/ml) | 7.57 | 6.61 | 7.45 | 7.69 |
| N | 6 | 6 | 6 | 6 |
| S. D. | 0.38 | 0.29 | 0.28 | 0.31 |

| GROUP | t | d. f. | p |
|---|---|---|---|
| A vs B | 4.90 | 10 | <0.001 |
| A vs C | 0.62 | 10 | >0.5 |
| A vs D | 0.60 | 10 | >0.5 |
| B vs C | 5.08 | 10 | <0.001 |
| B vs D | 6.20 | 10 | <0.001 |
| C vs D | 1.40 | 10 | >0.1 |

The bone mineral apposition rate was determined, as described previously, by measurement of the lower metaphysis of the left femur. The results are tabulated in Table Six and graphically depicted in FIG. 25.

TABLE SIX

Bone Mineral Apposition Rates of Ovariectomized Rats

| | Group A | Group B | Group C | Group D |
|---|---|---|---|---|
| Mean (μm/day) | 0.90 | 0.59 | 0.85 | 0.86 |
| N | 6 | 6 | 6 | 6 |
| S. D. | 0.12 | 0.07 | 0.07 | 0.09 |

| GROUP | t | d. f. | p |
|---|---|---|---|
| A vs B | 5.39 | 10 | <0.001 |
| A vs C | 0.87 | 10 | >0.5 |
| A vs D | 0.21 | 10 | >0.5 |
| B vs C | 6.29 | 10 | <0.001 |

TABLE SIX-continued

Bone Mineral Apposition Rates of Ovariectomized Rats

| B vs D | 5.93 | 10 | <0.001 |
|---|---|---|---|
| C vs D | 0.21 | 10 | >0.5 |

EXPERIMENTS INVOLVING OVARIECTOMIZED RATS AND THE NORMAL CHEMICALLY SYNTHESIZED POLYPEPTIDE, ADMINISTRATION OVER AN EIGHT WEEK PERIOD

Eight weeks after ovariectomization, five ovariectomized rats were injected subcutaneously with 100 μl of a 0.1% acetic acid solution containing 100 μg of the chemically synthesized peptide in which the N-terminal amino group was modified with an acetyl group (SEQ ID NO:12). This was done every 24 hours for eight weeks. On day 54, a tetracycline hydrochloride solution was injected intramuscularly into the right gluteus maximus of each rat so as to give 24 mg per Kg of body weight, as described previously. On day 56, a second dose of tetracycline hydrochloride was injected and the rats were sacrificed on the 57th day.

A second group of seven ovariectomized rats, was similarly treated with a 0.1% acetic acid solution containing no peptide over the same period. A third group of five rats, each of which had undergone the sham operation, was similarly treated with a 0.1% acetic acid solution containing no peptide over the same period. A fourth group of five intact rats was similarly treated with a 0.1% acetic acid solution containing no peptide over the same 8 week period. Two rats of the second group became ill during the 8 week period and were sacrificed prematurely.

Postmortem blood was taken by cardiac puncture and serum frozen until analyzed. An autopsy was performed on each rat. No obvious pathology was observed in the rats except for surgical scars and atrophy of the uterus and vagina of ovariectornized rats.

The right femurs were decalcified and calcium density determined as before. The results are presented in Table Seven and FIG. 26.

TABLE SEVEN

Right Femoral Calcium Concentration of Ovariectomized Rats

| | Group A | Group B | Group C | Group D |
|---|---|---|---|---|
| Mean (μmol/ml) | 7.37 | 6.89 | 7.69 | 7.87 |
| N | 5 | 5 | 5 | 5 |
| S. D. | 0.15 | 0.32 | 0.30 | 0.24 |

| GROUP | t | d. f. | p |
|---|---|---|---|
| A vs B | 3.85 | 6 | <0.005 |
| A vs C | 1.17 | 6 | >0.2 |
| A vs D | 3.01 | 6 | <0.01 |
| B vs C | 4.03 | 6 | <0.005 |
| B vs D | 5.41 | 6 | <0.001 |
| C vs D | 1.60 | 6 | >0.1 |

SYNTHESIS OF ANTIBODIES TO CHEMICALLY SYNTHESIZED PROTEIN (SEQ ID NO:11)

The chemically synthesized protein (SEQ ID NO:11) was coupled to KLH (keyhole limpet hemacyanin) with three different cross-linkers, as described below.

GLUTARALDEHYDE COUPLING

In 2.5 ml of a PBS solution made up of 2.7 mM KCl, 1.2 mM $KH_2PO_4$, 138 mM NaCl, 8.1 mM $Na_2HPO_4$, were diluted 5 mg of the peptide (SEQ ID NO:11) to obtain a final peptide concentration of 2 mg/ml. 10 mg of KLH were diluted in 5.0 ml PBS to obtain a final concentration of 2 mg/ml. To 1.25 ml of the KLH solution were added 1.25 ml of the peptide solution. Glutaraldehyde was added to a final concentration of 0.25%. The resultant solution was stirred for 1 hour at room temperature. After stirring, the solution was dialysed against 1 litre of PBS. The PBS was changed three times.

CARBODIIMIDE (EDC) COUPLING

Peptide and KLH solutions were prepared as described in the preceding section. To 1.25 ml KLH solution were added 1.25 ml peptide solution. To the resultant solution were added 2.5 mg of EDC. The solution was stirred constantly at room temperature for 4 hours and then dialysed against 1 litre of PBS. The PBS was changed three times.

M-MALEIMIDOBENZOYL-N-HYDROXYSUCCINIMIDE ESTER (MBS) COUPLING

To 500 µl of $H_2O$ were added 5 mg of the peptide and the pH was adjusted to 8.5 with NaOH, to obtain a final concentration of 10 mg/ml. Citraconic anhydride was diluted in $H_2O$ to a concentration of 10 mg/ml. 500 µl of the anhydride solution were added to the peptide solution 100 µl at a time with adjustment of the pH to 8.5 between each addition. The solution was then stirred constantly at room temperature for 1 hour. This was followed by the addition of 100 µl of 1M sodium phosphate buffer (pH 7.2) and then 900 µl of 100 mM sodium phosphate buffer (pH 7.2). Sulfo-MBS was diluted in $H_2O$ to a concentration of 25 mg/ml and 400 µl of this solution were added to the peptide solution to obtain an MBS concentration of about 5 mg/ml. This solution was stirred constantly at room temperature for 30 minutes. 6 µl of β-mercaptoethanol were added for a final β-mercaptoethanol concentration of 35 mM. The solution was stirred constantly at room temperature for 1 hour. KLH was dissolved in PBS at 3 mg/ml and 2.5 ml were added to the peptide solution. The solution was stirred constantly at room temperature for 3 hours and then dialysed against 1 litre of PBS, with three changes of the PBS. The final peptide concentration was about 1 mg/ml and the final KLH concentration was about 1.5 mg/ml.

ANTIBODY GENERATION

Rabbits were injected with the synthetic peptide solutions as follows. 250 µl each of the glutaraldehyde- and EDC-coupled peptide solutions were together mixed with 500 µl of Freund's adjuvant. This solution was injected intramuscularly into the rear legs of a rabbit, 500 µl per leg. The total amount of injected peptide was 0.5 mg. 500 µl of the synthetic peptide coupled to KLH with MBS were mixed with 500 µl of Freund's adjuvant. This solution was injected intramuscularly into the rear legs of another rabbit, 500 µl per leg. The total amount of injected peptide was 0.5 mg.

The synthetic peptide was loaded onto two lanes, 1.5 µg and 4 µg, of a gel (18% running, 5% stacking). The gel was blotted overnight at 30 V and blocked with 3% milk in PBS. The gel was incubated overnight with rabbit serum diluted 1:250 in 1% milk/PBS followed by incubation with goat anti-rabbit-alkaline phosphatase diluted 1:1000 for 1 hour. The gel was then developed with substrate. The synthetic peptide was seen by comasie blue staining. The peptide was detected by the second bleed of each rabbit and was not detected by the preimmune serum of either rabbit.

Interaction between immobilized peptide and serum antibodies was further studied through surface plasmon resonance using BIAcore™. The synthetic peptide was covalently immobilized on a dextran matrix by amine coupling. Rabbit serum of different dilutions were injected over the surface for five minutes and the amount of antibody bound to the immobilized peptide determined. The titer is defined as the last dilution of the serum giving a positive response, that is, greater than 50 Resonance Units. Using this approach, antibodies were found to be present in serum from both rabbits and the interaction can be blocked by preincubating the serum with the peptide. Antibodies in serum of the rabbits were found not to interact with an immobilized unrelated peptide.

EXPERIMENTS INVOLVING RATS AND ANTIBODIES TO THE CHEMICALLY SYNTHESIZED PEPTIDE

Antibody serum was prepared in 10 mM Tris.Cl at pH 7.4. Each of five rats received 100 µl of the solution by injection into the left gluteus maximus. Each rat of a second group of five rats was treated similarly, but with an additional injection of solution containing 45 µg of the polypeptide (SEQ ID NO:11) into the right gluteus maximus. Each rat of a third group of five rats received an injection of 100 µl of 10 mM Tris.Cl at pH 7.0.

Each of the fifteen rats was then injected as before with tetracycline hydrochloride, in the amount of 24 mg per Kg of body weight. A second dose of tetracycline hydrochloride was injected about 48 hours later. The rats were sacrificed after about another 24 hours.

The bone mineral apposition rate was determined by measurements, described above, of the lower right femoral metaphysis. The results are given in Table Eight and FIG. 27.

TABLE EIGHT

| Bone Mineral Apposition Rates in Rats Injected with Antibody to the Chemically Synthesized Peptide | | | |
|---|---|---|---|
| | Group A | Group B | Group C |
| Mean (µm/day) | 0.86 | 1.22 | 1.30 |
| S. D. | 0.02 | 0.08 | 0.11 |
| N | 5 | 5 | 5 |
| | t | d. f | p |
| Group A vs Group B | 8.06 | 8 | >0.2 |
| Group A vs Group C | 7.57 | 8 | <0.001 |
| Group B vs Group C | 1.24 | 8 | >0.2 |

Methodology and products can be thus be developed using antibody to the polypeptide for use in detecting the polypeptide with which the antibody binds. For example, antibody can be linked to or conjugated with any of several well known reporter systems set up to indicate positively binding of the polypeptide to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluorescence of a substance bound by the enzyme being assayed could be used. It will be appreciated that there are a number of reporter systems which may be used, according to the present invention, to detect the presence of a particular polypeptide. With standardized sample collection and treatment, polypeptide presence above a threshold amount in blood serum could well be determined.

Such a method based on antigenic response to the chemically synthesized human polypeptide (SEQ ID NO:11) could be developed and variants of the polypeptide obtained, as described above for amino acid substitution, deletion and addition, (and conjugates) could then be pre-screened as potential bone stimulating factors. Those that react positively with the antibody to the already known peptide could then be tested for bone stimulatory effects in vivo using the system described herein for rats, for example.

Such an antibody-linked reporter system could be used in a method for determining whether blood serum of a subject contains a deficient amount of the polypeptide. Given a normal threshold concentration of such a polypeptide in blood serum of a given type of subject, test kits could thus be developed.

EXPERIMENTS INVOLVING CHEMICALLY SYNTHESIZED HUMAN POLYPEPTIDE CONTAINING CYSTEINE→ALANINE SUBSTITUTION

A modified sequence (SEQ ID NO:13) of the chemically synthesized peptide (SEQ ID NO:11) obtained by substitution of the cysteine residue at position 13 by alanine was prepared by standard chemical procedures. Alanine residue is sterically similar to a reduced cysteine residue while rendering the polypeptide incapable of spontaneous dimerization. A tricine SDS electrophoretic gel of the modified and unmodified (normal) peptides is shown in FIG. 28.

Experiments were carried out on three groups of six rats weighing between 295 and 320 g. A 1 mg per ml solution of the modified peptide (SEQ ID NO:13) was prepared in 0.1% acetic acid. A 1 mg per ml solution of the normal peptide (SEQ ID NO:11) was prepared in 0.1% acetic acid. Each rat of a first of the groups had subcutaneously injected into its right thigh 0.1 ml of the modified peptide solution. Similarly, each rat of the second group was injected with 0.1 ml of the normal peptide solution. Each rat of the third group, the control group, was injected with 0.1 ml of 0.1% acetic acid solution. Immediately following these injections, each rat was injected intramuscularly with 24 mg per Kg body weight of tetracycline hydrochloride dissolved in 0.5 ml of water. A second dose of tetracycline hydrochloride was administered 48 hours later. The animals were sacrificed 24 hours after the second dose by $CO_2$ narcosis. The lower nietaphysis of the right femur was dissected out and fixed in a 10% aqueous solution of formaldehyde buffered at pH 7.2 by acetate buffer. Bone sections were prepared for measurement as described above.

The results are tabulated in Table Nine and graphically depicted in FIG. 29. As can be seen, the bone apposition rate for rats injected with the modified polypeptide is significantly greater than that for those of the control group but below the bone apposition rate shown for the rats injected with the normal peptide.

TABLE NINE

Comparison of the Group Arithmetic Means Among Groups Injected with Modified Peptide, Unmodified Peptide and Control

|  | Group A | Group B | Control Group |
|---|---|---|---|
| Mean (μm/day) | 1.67 μm/d | 1.35 μm/d | 1.02 μm/d |
| S. D. | 0.11 μm/d | 0.16 μm/d | 0.010 μm/d |
| N | 6 | 6 | 6 |
|  | t | d. f | p |
| Group A vs Control, Group C | 12.2 | 10 | <0.001 |
| Group B vs Control, Group C | 4.69 | 10 | <0.001 |
| Group B vs Group B | 3.97 | 10 | <0.005 |

It will of course be understood, without the intention of being limited thereby, that a variety of substitutions of amino acids is possible while "preserving" the three-dimensional structure responsible for the bone stimulatory effect of the polypeptides disclosed herein. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, cysteine, asparagine and glutamine could possibly be made. This being said, the linkage of the peptides together by the disulfide bridge might be of importance, and if so the lone cysteine residue should probably be held intact and other amino acids capable of forming a disulfide linkage not be substituted elsewhere in the sequence. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. These sorts of substitutions and interchanges are well known to those skilled in the art. Other substitutions might well be possible. It is thought that a polypeptide having an amino acid sequence with about 50% homology or more with the sequence identified as SEQ ID NO:11 (or SEQ ID NO:13) may well retain part or all of the bone stimulating activity of the sequence. In the context of this invention, a peptide containing an amino acid sequence that can be aligned with that of SEQ ID NO:II (or SEQ ID NO:13) such that at least about 50% of individual amino acid residues of the original sequence are conserved, allowing for a limited number of insertions or deletions between aligned sequences, would meet this criterion. Of course, it would also be expected that the greater percentage of homology, say 60%, 70%, 80%, 90%, or more, could increase the degree of retained bone stimulating activity.

Insofar as deletion of one or more amino acids is concerned, it is likely that deletions of a small number of amino acids from each end of the sequence might be possible. Further, symmetrical, or nearly symmetrical deletions would likely be the most possible to be made while retaining the three-dimensional configuration. Internal deletions, although likely to be possible to some limited extent, should be few, and should probably amount to no more than about five amino acids.

Additions of amino acids could very likely be made at the ends of the sequence, and as with deletions, symmetrical or nearly symmetrical additions to the carboxy and amino terminals are likely to be possible. Internal additions, although likely to be possible to some limited extent, should be few, and should probably amount to no more than about five amino acids, and preferably fewer.

Of the above-listed modifications to the sequence, terminal additions, deletions or substitutions are most likely to be most useful, as such a modification can serve a variety of functions: an identifying group as for use in a radioirnmunoassay; or a linking group, as examples.

A further advantage may be obtained through chimeric forms of the protein, as known in the art. A DNA sequence encoding the entire protein, or a portion of the protein, could thus be linked with a sequence coding for the C-terminal portion of E. coli β-galactosidase to produce a fusion protein, for example. An expression system for human respiratory syncytial virus glycoproteins F and G is described in U.S. Pat. No. 5,288,630, issued Feb. 22, 1994, and references cited therein, for example.

REFERENCES

1. Tam, C. S. 1989. The Pathogenesis of Metabolic Bone Disease: An Overview. In Metabolic Bone Disease: Cellular and Tissue Mechanisms. Eds. Tam, C. S., Heersche, J. N. M and Murray, T. M. CRC Press, Boca Ratong.
2. Parfitt A. M., Villanueva, A. R., Mathews, C. H. E., Aswani, S. A. 1980. Kinetics of matrix and mineral apposition in osteoporosis and renal osteodystrophy: relation of rate of turnover to cell morphology. Metab Bone Dis Rel Res, 2(S), 213.
3. Parfitt A. M. 1982. The coupling of bone formation to bone resorption: A critical analysis of the concept and of its relevance to the pathogenesis of osteoporosis. Metab Bone Dis Rel Res 4, 1.
4. Coccia, P. F., Krivit, W. Cerveuka, J., Clawson, C., Kersey, J., Kim, T. H., Nesbit, M. E., Ramsey, N. K. C., Warkeutin, P. I., Teitelbaum, S. L., Kahn, A. J., Brown, D. M. 1980. Successful bone marrow transplantation for infantile malignant osteopetrosis. New Eng J. Med, 320, 701.
5. Marks, S. C. Jr., Walker, D. G. 1981. The hematogenous origin of osteoclast: evidence form osteopetrotic (microphthalamic) mice treated with spleen cell from geige mouse donor. Am J Anat 161,1.
6. Owen M. 1985. Lineage of osteogenic cells and their relationship to the stromal system. In Bone and Mineral Research, Vol 3, Ed. Peck W. A. Amsterdam 1.
7. Yamamoto, I. 1985. Regulation of receptors for parathyroid hormone in rat osteosarcoma cells. J.J.B.M. 3,38.
8. Canalis, E. 1986. Interleulin-1 has independent effects on deoxyribonucleic acid and collagen synthesis in cultures of rat calvariae, Endocrinol 118, 74.
9. Centrella, M., Canalis, E. 1985. Transforming and non-transforming growth factor are present in medium conditioned by fetal rat calvariae. Proc Natl Acad Sci, U.S.A. 82, 7355.
10. Canalis, E. 1985. Effect of growth factors on bone cell replication and differentiation. Clin Orthop 183, 246.
11. Chyun, Y. S., Raisz, L. G. 1984. Stimulation of bone formation by prostaglandin E2. Prostaglandins, 27, 97.
12. Canalis, E. 1980. Effects of insulin-like growth factor 1 on DNA and protein synthesis in cultured rat calvariae. J Clin Invest, 66, 709.
13. Klein, D. C., Raisz, L. G. 1970. Prostaglandins: stimulation of bone resorption in tissue culture. Endocrinol 86 1436.
14. Tashjian A. H., Jr., Voekel, E. F., Lazarro, M., Singer, F. R., Roberts, A., Derynck, R., Winkler, M. E., Levine, L. 11985, a and b human transforming growth factors stimulate protaglandin production and bone resorption in cultured mouse calvariae. Proc Natl Acad Sci, U.S.A. 82, 4535.
15. Chen, T. L., Cone, C. M., Morey-Holton, E., Feldman, D. 1982. Glucocorticoid regulation of 1,25(OH)$_2$D3 receptors on cultured mouse bone cells. J. Biol Chem 257, 13563.
16. Roodman, G. D. 1992. Perspectives:Interleukin-6: An osteotropic factor. J. Bone Miner Res, 7, 475.
17. Segre G. V. 1990 Secretion, metabolism and circulating heterogeneity of parathyroid hormone. In Primer in Metabolic Bone diseases and Disorders of Mineral Metabolism. First Edition. ed. Favus, M. J., Kelseyville, Calif.
18. Selye H. 1933. On the stimulation of new bone formation with parathyroid extract and irradiated ergosterol. Endocrinol 16, 547.
19. Aitken R. E., Kerr J. L., Loyd H. M. 1964. Primary hyperparathyroidism with osteosclerosis and calcification in articular cartilage. Am J Med 37, 813.
20. Connor T. B., Freijances J., Stoner R. E., Martin L. G., Jowsey J. 1973. Generalized osteosclerosis in primary hyperparathyroidism. Trans Am Clin Climatol Assoc 85, 185.
21. Gennant H. K., Baron J. M., Paloyan E., Jowsey J. 1975. Osteosclerosis in primary hyperparathyroidism. Am J Med 59, 104.
22. Kalu, D. N., Pennock J., Doyle, F. H., Foster G. V. 1970. Parathyroid hormone and experimental osteosclerosis. Lancet 1, 1363.
23. Tam C. S., Harrison J. E., Reed R., Cruickshank B. 1978. Bone apposition rate as an index of bone metabolism. Metabolism 27, 143.
24. Tam C. S., Bayley T. A., Harrison J. E., Murray T. M., Birkin B. L., Thompson D. 1978. Bone biopsy in the diagnosis of primary hyperparathyroidism. In Copp D. H., Talmage R. V. (eds) Endocrinology of Calcium Metabolism. Excerpta Medica, Amsterdam, p 427 (Abstract).
25. Tam, C. S., Heersche, J. N. M., Murray, T. M., Parsons J. A. 1982. Paralhyroid hormone stimulates the apposition rate independent of its resorptive action: Differential effects of intermittent and continuous administration. Endocrinol 110, 506.
26. Tam, C. S., Anderson, W. 1980. Tetracycline labelling of bone in vivo. Calcif Tiss Res 30, 121.
27. Molecular Cloning, A Laboratory Manual (Second Edition) Sambroot J., Fritsch E. F., Maniatis T., Cold Spring Harbor Press, 1989.
28. Organic Chemistry, ed. Loudon, G. Marc (Ed), Addison-Wesley Publishing Company, Massachusetts, 1984.

---

What is claimed is:

1. An isolated polypeptide having the amino acid sequence (SEQ ID NO:11) NH$_2$-Gly-Ile-Gly-Lys-Arg-Thr-Asn-Glu-His-Thr-Ala-Asp-Cys-Lys-Ile-Lys- Pro-Asn-Thr-Leu-His-Lys-Lys-Ala-Ala-Glu-Thr-Leu-Met-Val-Leu-Asp-Gln-Asn-Gln-Pro-CO$_2$H, or a conservatively substituted variant thereof exhibiting mammalian bone stimulators activity.

2. A chimeric bone stimulating factor comprising the amino acid sequence set forth in claim 1.

3. A polypeptide of claim 1 wherein the polypeptide has at least about 50% homology with SEQ ID NO:11.

4. A polypeptide of claim 1 wherein the polypeptide has at least about 60% homology with SEQ ID NO:11.

5. A polypeptide of claim 1 wherein the polypeptide has at least about 70% homology with SEQ ID NO:11.

6. A polypeptide of claim 1 wherein the polypeptide has at least about 80% homology with SEQ ID NO:11.

7. A polypeptide of claim 1 wherein the polypeptide has at least about 90% homology with SEQ ID NO:11.

8. A polypeptide of claim 1 wherein at least one non-polar aliphatic neutral amino acid of SEQ ID NO:11 is substituted by a different non-polar aliphatic neutral amino acid.

9. A polypeptide of claim 1 wherein at least one polar aliphatic neutral amino acid of SEQ ID NO:11 is substituted by a different polar aliphatic neutral amino acid.

10. A polypeptide of claim 1 wherein at least one charged acidic amino acid of SEQ ID NO:11 is substituted by a different charged acidic amino acid.

11. A polypeptide of claim 1 wherein at least one charged basic amino acid of SEQ ID NO:11 is substituted by a different charged basic amino acid.

12. An isolated dimeric polypeptide wherein each monomer of polypeptide contains the following amino acid sequence (SEQ ID NO:11) $NH_2$-Gly-Ile-Gly-Lys-Arg-Thr-Asn-Glu-His-Thr-Ala-Asp-Cys-Lys-Ile-Lys-Pro-Asn-Thr-Leu-His-Lys-Lys-Ala-Ala-Glu-Thr-Leu-Met-Val-Leu-Asp-Gln-Asn-Gln- Pro-$CO_2$H; wherein the monomers are linked to each other by a disulfide bridge between the cysteine residues of the respective sequences, or a conservatively substituted variant thereof exhibiting mammalian bone stimulatory activity.

13. A polypeptide of claim 12 wherein the polypeptide has at least about 50% homology with SEQ ID NO:11.

14. A polypeptide of claim 12 wherein the polypeptide has at least about 60% homology with SEQ ID NO:11.

15. A polypeptide of claim 12 wherein the polypeptide has at least about 70% homology with SEQ ID NO:11.

16. A polypeptide of claim 12 wherein the polypeptide has at least about 80% homology with SEQ ID NO:11.

17. A polypeptide of claim 12 wherein the polypeptide has at least about 90% homology with SEQ ID NO:11.

18. A polypeptide of claim 12 wherein at least one non-polar aliphatic neutral amino acid of SEQ ID NO:11 is substituted by a different non-polar aliphatic neutral amino acid.

19. A polypeptide of claim 12 wherein at least one polar aliphatic neutral amino acid of SEQ ID NO:11 is substituted by a different polar aliphatic neutral amino acid.

20. A polypeptide of claim 12 wherein at least one charged acidic amino acid of SEQ ID NO:11 is substituted by a different charged acidic amino acid.

21. A polypeptide of claim 12 wherein at least one charged basic amino acid of SEQ ID NO:11 is substituted by a different charged basic amino acid.

22. An isolated polypeptide exhibiting bone stimulatory activity in mammals, the polypeptide comprising a monomer having the following amino acid sequence (SEQ ID NO:11) N-2Gly-Ile-Gly-Lys-Arg-Thr-Asn-Glu-His-Thr-Ala-Asp-Cys-Lys-Ile-Lys-Pro-Asn-Thr- Leu-His-Lys-Lys-Ala-Ala-Glu-Thr-Leu-Met-Val-Leu-Asp-Gln-Asn-Gln-Pro-$CO_2$H and dimers thereof; wherein the monomers are linked to each other by a disulfide bridge between the cysteine residues of the respective sequences, or a conservatively substituted variant thereof exhibiting mammalian bone stimulators activity.

23. A polypeptide of claim 22 wherein the polypeptide has at least about 50% homology with SEQ ID NO:11.

24. A polypeptide of claim 22 wherein the polypeptide has at least about 60% homology with SEQ ID NO:11.

25. A polypeptide of claim 22 wherein the polypeptide has at least about 70% homology with SEQ ID NO:11.

26. A polypeptide of claim 22 wherein the polypeptide has at least about 80% homology with SEQ ID NO:11.

27. A polypeptide of claim 22 wherein the polypeptide has at least about 90% homology with SEQ ID NO:11.

28. A polypeptide of claim 22 wherein at least one non-polar aliphatic neutral amino acid of SEQ ID NO:11 is substituted by a different non-polar aliphatic neutral amino acid.

29. A polypeptide of claim 22 wherein at least one polar aliphatic neutral amino acid of SEQ ID NO:11 is substituted by a different polar aliphatic neutral amino acid.

30. A polypeptide of claim 22 wherein at least one charged acidic amino acid of SEQ ID NO:11 is substituted by a different charged acidic amino acid.

31. A polypeptide of claim 22 wherein at least one charged basic amino acid of SEQ ID NO:11 is substituted by a different charged basic amino acid.

32. A polypeptide having the amino acid sequence (SEQ ID NO:13) $NH_2$-Gly-Ile-Gly-Lys-Arg-Thr-Asn-Glu- His-Thr-Ala-Asp-Ala-Lys-Ile-Lys-Pro-Asn-Thr-Leu-His-Lys-Lys-Ala-Ala-Glu-Thr-Leu-Met-Val-Leu-Asp-Gln-Asn-Gln-Pro-$CO_2$H, or a conservatively substituted variant thereof exhibiting mammalian bone stimulators activity.

33. A chimeric bone stimulating factor comprising the amino acid sequence set forth in claim 32.

34. A polypeptide of claim 32 wherein the polypeptide has at least about 60% homology with SEQ ID NO:11.

35. A polypeptide of claim 32 wherein the polypeptide has at least about 70% homology with SEQ ID NO:11.

36. A polypeptide of claim 32 wherein the polypeptide has at least about 80% homology with SEQ ID NO:11.

37. A polypeptide of claim 32 wherein the polypeptide has at least about 90% homology with SEQ ID NO:11.

38. A polypeptide of claim 32 wherein at least one non-polar aliphatic neutral amino acid of SEQ ID NO:11 is substituted by a different non-polar aliphatic neutral amino acid.

39. A polypeptide of claim 32 wherein at least one polar aliphatic neutral amino acid of SEQ ID NO:11 is substituted by a different polar aliphatic neutral amino acid.

40. A polypeptide of claim 32 wherein at least one charged acidic amino acid of SEQ ID NO:11 is substituted by a different charged acidic amino acid.

41. A polypeptide of claim 32 wherein at least one charged basic amino acid of SEQ ID NO:11 is substituted by a different charged basic amino acid.

42. A method of increasing bone growth in a mammal by administering a therapeutically effective amount of a polypeptide having the amino sequence (SEQ ID NO:11) $NH_2$-Gly-Ile-Gly-Lys-Arg-Thr-Asn-Glu-His-Thr-Ala-Asp-Cys-Lys-Ile- Lys-Pro-Asn-Thr-Leu-His-Lys-Lys-Ala-Ala-Glu-Thr-Leu-Met-Val-Leu-Asp-Gln-Asn-Gln-Pro-$CO_2$H, or a conservatively substituted variant thereof exhibiting mammalian bone stimulators activity.

43. A method of increasing bone growth in a mammal by administering a therapeutically effective amount of a polypeptide having the amino sequence (SEQ ID NO:13) $NH_2$-Gly-Ile-Gly-Lys-Arg-Thr-Asn-Glu-His-Thr-Ala-Asp-Ala-Lys-Ile- Lys-Pro-Asn-Thr-Leu-His-Lys-Lys-Ala-Ala-Glu-Thr-Leu-Met-Val-Leu-Asp-Gln-Asn-Gln-Pro-$CO_2$H, or a conservatively substituted variant thereof exhibiting mammalian bone stimulatory activity.

44. A substantially pure circulatory nolypeptide isolated from blood serum of a rat, which polypeptide induces an increased bone apposition rate and has the following N-terminal amino acid sequence (SEQ ID NO:1):Gly-Pro-Gly-Gly-Ala-Gly-Thr-Lys-Pro-Ile.

45. A method of producing the polypeptide having an N-terminal amino acid sequence of (SEQ ID NO:1) Gly- Pro-Gly-Gly-Ala-Gly-Glu-Thr-Lys-Pro-Ile from rat blood serum, comprising the steps of:
- obtaining a protein fraction of the blood serum;
- removing from the fraction proteins having a molecular weight greater than about 30,000 daltons; and
- isolating the polypeptide.

46. The method of claim 45 wherein isolating the polypeptide comprises collecting the polypeptide from a reverse phase high performance liquid chromatography column.

47. The method of claim 46 wherein collecting the polypeptide includes eluting the polypeptide from a reverse phase high performance liquid chromatography column packed with silica gel having three carbon chain side groups attached thereto using an elution solvent comprising at least about 52 to 53 percent acetonitrile.

48. A method of obtaining a polypeptide from a mammal which stimulates bone growth in a mammal, comprising the steps of:
- (a) feeding the mammal a calcium deficient diet to increase the level of the polypeptide in the blood serum of the mammal;
- (b) isolating a sample of the blood serum of the mammal; and
- (c) collecting from the sample in substantially pure form a polypeptide having the N-terminal amino acid sequence (SEQ ID NO:1) Gly-Pro-Gly-Gly-Ala-Gly-Glu-Thr-Lys-Pro-Ile.

49. An isolated polypeptide having the amino acid sequence (SEQ ID NO:11) $NH_2$-Gly-Ile-Gly-Lys-Arg-Thr-Asn-Glu-His-Thr-Ala-Asp-Cys-Lys-Ile-Lys-Pro-Asn-Thr-Leu-His-Lys-Lys-Ala-Ala-Glu-Thr-Leu-Met-Val-Leu-Asp-Gln-Asn-Gln-Pro-$CO_2H$, or a conservatively substituted variant having at least about 50% homology with SEQ ID NO:11 which stimulates bone growth in a mammal.

50. A polypeptide of claim 49 wherein the polypeptide has at least about 60% homology with SEQ ID NO:11.

51. A polypeptide of claim 49 wherein the polypeptide has at least about 70% homology with SEQ ID NO:11.

52. A polypeptide of claim 49 wherein the polypeptide has at least about 80% homology with SEQ ID NO:11.

53. A polypeptide of claim 49 wherein the polypeptide has at least about 90% homology with SEQ ID NQ:11.

54. A polypeptide of claim 49 wherein at least one non-polar aliphatic neutral amino acid of SEQ ID NO:11 is substituted by a different non-polar aliphatic neutral amino acid.

55. A polypeptide of claim 49 wherein at least one polar aliphatic neutral amino acid of SEQ ID NO:11 is substituted by a different polar aliphatic neutral amino acid.

56. A polypeptide of claim 49 wherein at least one charged acidic amino acid of SEQ ID NO:11 is substituted by a different charged acidic amino acid.

57. A polypeptide of claim 49 wherein at least one charged basic amino acid of SEQ ID NO:11 is substituted by a different charged basic amino acid.

* * * * *

UNITED STATES PATENT AND TRADEMARK OFFICE
CERTIFICATE OF CORRECTION

PATENT NO. : 5,786,327
DATED : July 28, 1998
INVENTOR(S) : Cherk Shing TAM

It is certified that error appears in the above-identified patent and that said Letters Patent is hereby corrected as shown below:

Please note and correct, Column 41, line 66, Claim 1, delete "bone stimulators activity", insert --bone stimulatory activity--; Column 43, line 60, Claim 22, delete "bone stimulators activity", insert --bone stimulatory activity--; Column 44, line 21, Claim 32, delete "bone stimulators activity", insert --bone stimulatory activity--. Column 44, line 52, Claim 42, delete "bone stimulators activity", insert --bone stimulatory activity--.

Signed and Sealed this

Second Day of March, 1999

Attest:

Attesting Officer

Q. TODD DICKINSON

Acting Commissioner of Patents and Trademarks